US012067804B2

(12) United States Patent
Assouline et al.

(10) Patent No.: US 12,067,804 B2
(45) Date of Patent: Aug. 20, 2024

(54) TRUE SIZE EYEWEAR EXPERIENCE IN REAL TIME

(71) Applicant: Snap Inc., Santa Monica, CA (US)

(72) Inventors: Avihay Assouline, Tel Aviv (IL);
Itamar Berger, Hod Hasharon (IL);
Jean Luo, Los Angeles, CA (US);
Matan Zohar, Rishon LeZion (IL)

(73) Assignee: Snap Inc., Santa Monica, CA (US)

( * ) Notice: Subject to any disclaimer, the term of this patent is extended or adjusted under 35 U.S.C. 154(b) by 708 days.

(21) Appl. No.: 17/208,208

(22) Filed: Mar. 22, 2021

(65) Prior Publication Data

US 2022/0300728 A1 Sep. 22, 2022

(51) Int. Cl.
*G06V 40/16* (2022.01)
*A61B 90/00* (2016.01)
(Continued)

(52) U.S. Cl.
CPC ............ *G06V 40/171* (2022.01); *G06F 3/011* (2013.01); *G06Q 30/0631* (2013.01);
(Continued)

(58) Field of Classification Search
CPC ........... G06T 2207/30201; G06T 19/20; G06T 17/20; G06T 13/40; G06T 7/0012; G06T 2207/30196; G06T 7/70; G06T 19/006; G06T 2207/10028; G06T 2219/2016; G06T 2219/2004; G06T 7/50; G06T 3/0093; G06T 7/149; G06T 3/40; G06T 2210/44; G06T 9/001; G06T 2207/20101;
(Continued)

(56) References Cited

U.S. PATENT DOCUMENTS 5,880,731 A 3/1999 Liles et al.
6,023,270 A 2/2000 Brush, II et al.
(Continued)

FOREIGN PATENT DOCUMENTS

CN 109003298 A * 12/2018
CN 109863532 6/2019
(Continued)

OTHER PUBLICATIONS

Search machine translation of CN-109003298-A to Ding et al., Virtual Glasses Matching Method And System, translated Nov. 25, 2023, 19 pages. (Year: 2023).*
(Continued)

*Primary Examiner* — Matthew C Bella
*Assistant Examiner* — Dennis Rosario
(74) *Attorney, Agent, or Firm* — Schwegman Lundberg & Woessner, P.A.

(57) ABSTRACT

Methods and systems are disclosed for performing operations comprising: receiving, by one or more processors, an image that includes a depiction of a face of a user; computing a real-world scale of the face of the user based on a selected subset of landmarks of the face of the user; obtaining an augmented reality graphical element comprising augmented reality eyewear; scaling the augmented reality graphical element based on the computed real-world scale of the face; and positioning the scaled augmented reality graphical element within the image on the face of the user.

20 Claims, 13 Drawing Sheets

(51) Int. Cl.
*G06F 3/01* (2006.01)
*G06Q 30/0601* (2023.01)
*G06T 19/00* (2011.01)
*G06T 19/20* (2011.01)
*G06V 20/00* (2022.01)
*G06V 20/20* (2022.01)
*H04N 13/00* (2018.01)

(52) U.S. Cl.
CPC ............ *G06T 19/006* (2013.01); *G06T 19/20* (2013.01); *G06V 20/00* (2022.01); *G06V 20/20* (2022.01); *G06V 40/165* (2022.01); *A61B 2090/365* (2016.02); *G06T 2207/10028* (2013.01); *G06T 2219/2004* (2013.01); *G06T 2219/2016* (2013.01); *G06T 2219/2021* (2013.01); *G06T 2219/2024* (2013.01); *H04N 2013/0081* (2013.01)

(58) Field of Classification Search
CPC ....... G06T 3/0068; G06T 19/00; G06T 7/593; G06T 7/33; G06T 2207/30204; G06T 7/521; G06T 7/536; G06T 2207/10021; G06T 7/73; G06T 7/74; G06T 7/246; G06T 7/248; G06T 3/14; G06T 7/0014; G06T 7/30; G06T 7/337; G06V 40/171; G06V 40/165; G06V 40/168; G06V 40/161; G06V 20/20; G06V 40/16; G06V 40/18; G06V 40/174; G06V 40/178; G06V 10/462; G06V 10/754; G06V 10/755; G06V 40/193; G06V 10/245; G06V 40/169; G06V 40/10; G06V 20/46; G06V 2201/12; G06V 10/7715; G06V 10/40; G06V 40/173; G06V 40/175; G06V 40/176; G06V 10/22; G06V 30/1912; G06V 30/191; G06F 3/011; G06F 3/012; G06F 3/013; H04N 23/611; H04N 2013/0081; H04N 13/383; H04N 5/2628; H04N 13/128; H04N 13/122; H04N 21/23418; H04N 13/117; H04N 19/54; H04N 23/671; G02B 2027/0178; G02C 13/003; G02C 7/027; A61B 2090/502; A61B 5/0077; A61B 2090/365; A61B 2090/363; A61B 90/39; A61B 2090/3966; A61B 2090/3945; A61B 5/744

See application file for complete search history.

(56) References Cited

U.S. PATENT DOCUMENTS

| | | | |
|---|---|---|---|
| 6,223,165 B1 | 4/2001 | Lauffer | |
| 6,772,195 B1 | 8/2004 | Hatlelid et al. | |
| 6,842,779 B1 | 1/2005 | Nishizawa | |
| 7,342,587 B2 | 3/2008 | Danzig et al. | |
| 7,468,729 B1 | 12/2008 | Levinson | |
| 7,636,755 B2 | 12/2009 | Blattner et al. | |
| 7,639,251 B2 | 12/2009 | Gu et al. | |
| 7,775,885 B2 | 8/2010 | Van et al. | |
| 7,859,551 B2 | 12/2010 | Bulman et al. | |
| 7,885,931 B2 | 2/2011 | Seo et al. | |
| 7,925,703 B2 | 4/2011 | Dinan et al. | |
| 8,088,044 B2 | 1/2012 | Tchao et al. | |
| 8,095,878 B2 | 1/2012 | Bates et al. | |
| 8,108,774 B2 | 1/2012 | Finn et al. | |
| 8,117,281 B2 | 2/2012 | Robinson et al. | |
| 8,130,219 B2 | 3/2012 | Fleury et al. | |
| 8,146,005 B2 | 3/2012 | Jones et al. | |
| 8,151,191 B2 | 4/2012 | Nicol | |
| 8,384,719 B2 | 2/2013 | Reville et al. | |
| RE44,054 E | 3/2013 | Kim | |
| 8,396,708 B2 | 3/2013 | Park et al. | |
| 8,425,322 B2 | 4/2013 | Gillo et al. | |
| 8,458,601 B2 | 6/2013 | Castelli et al. | |
| 8,462,198 B2 | 6/2013 | Lin et al. | |
| 8,484,158 B2 | 7/2013 | Deluca et al. | |
| 8,495,503 B2 | 7/2013 | Brown et al. | |
| 8,495,505 B2 | 7/2013 | Smith et al. | |
| 8,504,926 B2 | 8/2013 | Wolf | |
| 8,559,980 B2 | 10/2013 | Pujol | |
| 8,564,621 B2 | 10/2013 | Branson et al. | |
| 8,564,710 B2 | 10/2013 | Nonaka et al. | |
| 8,581,911 B2 | 11/2013 | Becker et al. | |
| 8,597,121 B2 | 12/2013 | del Valle | |
| 8,601,051 B2 | 12/2013 | Wang | |
| 8,601,379 B2 | 12/2013 | Marks et al. | |
| 8,632,408 B2 | 1/2014 | Gillo et al. | |
| 8,648,865 B2 | 2/2014 | Dawson et al. | |
| 8,659,548 B2 | 2/2014 | Hildreth | |
| 8,683,354 B2 | 3/2014 | Khandelwal et al. | |
| 8,692,830 B2 | 4/2014 | Nelson et al. | |
| 8,810,513 B2 | 8/2014 | Ptucha et al. | |
| 8,812,171 B2 | 8/2014 | Filev et al. | |
| 8,832,201 B2 | 9/2014 | Wall | |
| 8,832,552 B2 | 9/2014 | Arrasvuori et al. | |
| 8,839,327 B2 | 9/2014 | Amento et al. | |
| 8,890,926 B2 | 11/2014 | Tandon et al. | |
| 8,892,999 B2 | 11/2014 | Nims et al. | |
| 8,924,250 B2 | 12/2014 | Bates et al. | |
| 8,963,926 B2 | 2/2015 | Brown et al. | |
| 8,989,786 B2 | 3/2015 | Feghali | |
| 9,086,776 B2 | 7/2015 | Ye et al. | |
| 9,105,014 B2 | 8/2015 | Collet et al. | |
| 9,241,184 B2 | 1/2016 | Weerasinghe | |
| 9,256,860 B2 | 2/2016 | Herger et al. | |
| 9,298,257 B2 | 3/2016 | Hwang et al. | |
| 9,314,692 B2 | 4/2016 | Konoplev et al. | |
| 9,330,483 B2 | 5/2016 | Du et al. | |
| 9,357,174 B2 | 5/2016 | Li et al. | |
| 9,361,510 B2 | 6/2016 | Yao et al. | |
| 9,378,576 B2 | 6/2016 | Bouaziz et al. | |
| 9,402,057 B2 | 7/2016 | Kaytaz et al. | |
| 9,412,192 B2 | 8/2016 | Mandel et al. | |
| 9,460,541 B2 | 10/2016 | Li et al. | |
| 9,489,760 B2 | 11/2016 | Li et al. | |
| 9,503,845 B2 | 11/2016 | Vincent | |
| 9,508,197 B2 | 11/2016 | Quinn et al. | |
| 9,544,257 B2 | 1/2017 | Ogundokun et al. | |
| 9,576,400 B2 | 2/2017 | Van Os et al. | |
| 9,589,357 B2 | 3/2017 | Li et al. | |
| 9,592,449 B2 | 3/2017 | Barbalet et al. | |
| 9,648,376 B2 | 5/2017 | Chang et al. | |
| 9,697,635 B2 | 7/2017 | Quinn et al. | |
| 9,706,040 B2 | 7/2017 | Kadirvel et al. | |
| 9,723,369 B2 | 8/2017 | Kim et al. | |
| 9,744,466 B2 | 8/2017 | Fujioka | |
| 9,746,990 B2 | 8/2017 | Anderson et al. | |
| 9,749,270 B2 | 8/2017 | Collet et al. | |
| 9,792,714 B2 | 10/2017 | Li et al. | |
| 9,839,844 B2 | 12/2017 | Dunstan et al. | |
| 9,883,838 B2 | 2/2018 | Kaleal, III et al. | |
| 9,898,849 B2 | 2/2018 | Du et al. | |
| 9,911,073 B1 | 3/2018 | Spiegel et al. | |
| 9,936,165 B2 | 4/2018 | Li et al. | |
| 9,959,037 B2 | 5/2018 | Chaudhri et al. | |
| 9,980,100 B1 | 5/2018 | Charlton et al. | |
| 9,990,373 B2 | 6/2018 | Fortkort | |
| 10,039,988 B2 | 8/2018 | Lobb et al. | |
| 10,097,492 B2 | 10/2018 | Tsuda et al. | |
| 10,116,598 B2 | 10/2018 | Tucker et al. | |
| 10,155,168 B2 | 12/2018 | Blackstock et al. | |
| 10,242,477 B1 | 3/2019 | Charlton et al. | |
| 10,242,503 B2 | 3/2019 | McPhee et al. | |
| 10,262,250 B1 | 4/2019 | Spiegel et al. | |
| 10,362,219 B2 | 7/2019 | Wilson et al. | |
| 10,475,225 B2 | 11/2019 | Park et al. | |
| 10,504,266 B2 | 12/2019 | Blattner et al. | |
| 10,573,048 B2 | 2/2020 | Ni et al. | |
| 10,657,701 B2 | 5/2020 | Osman et al. | |

(56) References Cited

U.S. PATENT DOCUMENTS

| | | |
|---|---|---|
| 11,562,548 B2 | 1/2023 | Assouline et al. |
| 2002/0067362 A1 | 6/2002 | Agostino Nocera et al. |
| 2002/0169644 A1 | 11/2002 | Greene |
| 2005/0162419 A1 | 7/2005 | Kim et al. |
| 2005/0206610 A1 | 9/2005 | Cordelli |
| 2006/0294465 A1 | 12/2006 | Ronen et al. |
| 2007/0113181 A1 | 5/2007 | Blattner et al. |
| 2007/0168863 A1 | 7/2007 | Blattner et al. |
| 2007/0176921 A1 | 8/2007 | Iwasaki et al. |
| 2008/0158222 A1 | 7/2008 | Li et al. |
| 2009/0016617 A1 | 1/2009 | Bregman-amitai et al. |
| 2009/0055484 A1 | 2/2009 | Vuong et al. |
| 2009/0070688 A1 | 3/2009 | Gyorfi et al. |
| 2009/0099925 A1 | 4/2009 | Mehta et al. |
| 2009/0106672 A1 | 4/2009 | Burstrom |
| 2009/0158170 A1 | 6/2009 | Narayanan et al. |
| 2009/0177976 A1 | 7/2009 | Bokor et al. |
| 2009/0202114 A1 | 8/2009 | Morin et al. |
| 2009/0215533 A1 | 8/2009 | Zalewski et al. |
| 2009/0265604 A1 | 10/2009 | Howard et al. |
| 2009/0300525 A1 | 12/2009 | Jolliff et al. |
| 2009/0303984 A1 | 12/2009 | Clark et al. |
| 2010/0011422 A1 | 1/2010 | Mason et al. |
| 2010/0023885 A1 | 1/2010 | Reville et al. |
| 2010/0115426 A1 | 5/2010 | Liu et al. |
| 2010/0162149 A1 | 6/2010 | Sheleheda et al. |
| 2010/0172567 A1 | 7/2010 | Prokoski |
| 2010/0203968 A1 | 8/2010 | Gill et al. |
| 2010/0227682 A1 | 9/2010 | Reville et al. |
| 2011/0093780 A1 | 4/2011 | Dunn |
| 2011/0115798 A1 | 5/2011 | Nayar et al. |
| 2011/0148864 A1 | 6/2011 | Lee et al. |
| 2011/0239136 A1 | 9/2011 | Goldman et al. |
| 2012/0113106 A1 | 5/2012 | Choi et al. |
| 2012/0124458 A1 | 5/2012 | Cruzada |
| 2012/0130717 A1 | 5/2012 | Xu et al. |
| 2013/0103760 A1 | 4/2013 | Golding et al. |
| 2013/0201187 A1 | 8/2013 | Tong et al. |
| 2013/0249948 A1 | 9/2013 | Reitan |
| 2013/0257877 A1 | 10/2013 | Davis |
| 2014/0043329 A1 | 2/2014 | Wang et al. |
| 2014/0055554 A1 | 2/2014 | Du et al. |
| 2014/0125678 A1 | 5/2014 | Wang et al. |
| 2014/0129343 A1 | 5/2014 | Finster et al. |
| 2014/0147022 A1 | 5/2014 | Zhou et al. |
| 2015/0055085 A1* | 2/2015 | Fonte .................. G02C 7/027 700/98 |
| 2015/0206349 A1 | 7/2015 | Rosenthal et al. |
| 2016/0134840 A1 | 5/2016 | Mcculloch |
| 2016/0171287 A1 | 6/2016 | Surkov et al. |
| 2016/0234149 A1 | 8/2016 | Tsuda et al. |
| 2017/0080346 A1 | 3/2017 | Abbas |
| 2017/0087473 A1 | 3/2017 | Siegel et al. |
| 2017/0113140 A1 | 4/2017 | Blackstock et al. |
| 2017/0118145 A1 | 4/2017 | Aittoniemi et al. |
| 2017/0199855 A1 | 7/2017 | Fishbeck |
| 2017/0235848 A1 | 8/2017 | Van Deusen et al. |
| 2017/0310934 A1 | 10/2017 | Du et al. |
| 2017/0312634 A1 | 11/2017 | Ledoux et al. |
| 2018/0047200 A1 | 2/2018 | O'hara et al. |
| 2018/0113587 A1 | 4/2018 | Allen et al. |
| 2018/0115503 A1 | 4/2018 | Baldwin et al. |
| 2018/0268472 A1* | 9/2018 | Vilcovsky .............. G06N 5/047 |
| 2018/0293754 A1 | 10/2018 | Ahuja et al. |
| 2018/0315076 A1 | 11/2018 | Andreou |
| 2018/0315133 A1 | 11/2018 | Brody et al. |
| 2018/0315134 A1 | 11/2018 | Amitay et al. |
| 2018/0374231 A1 | 12/2018 | Znamenskiy et al. |
| 2019/0001223 A1 | 1/2019 | Blackstock et al. |
| 2019/0057616 A1 | 2/2019 | Cohen et al. |
| 2019/0147676 A1 | 5/2019 | Madzhunkov et al. |
| 2019/0179405 A1 | 6/2019 | Sun et al. |
| 2019/0188920 A1 | 6/2019 | Mcphee et al. |
| 2020/0219326 A1 | 7/2020 | Goldberg et al. |
| 2020/0252217 A1 | 8/2020 | Mathieu |
| 2021/0110161 A1* | 4/2021 | Wang .................. G06V 40/165 |
| 2021/0392175 A1 | 12/2021 | Gronau et al. |
| 2022/0301272 A1 | 9/2022 | Assouline et al. |
| 2023/0120037 A1 | 4/2023 | Assouline et al. |

FOREIGN PATENT DOCUMENTS

| | | |
|---|---|---|
| CN | 110168478 | 8/2019 |
| CN | 117043829 | 11/2023 |
| CN | 117083641 A | 11/2023 |
| EP | 2184092 | 5/2010 |
| FR | 3024911 | 2/2016 |
| JP | 2001230801 | 8/2001 |
| JP | 5497931 | 3/2014 |
| JP | 2017194301 A * | 10/2017 |
| KR | 101445263 | 9/2014 |
| WO | 2003094072 | 11/2003 |
| WO | 2004095308 | 11/2004 |
| WO | 2006107182 | 10/2006 |
| WO | 2007134402 | 11/2007 |
| WO | 2012139276 | 10/2012 |
| WO | 2013027893 | 2/2013 |
| WO | 2013152454 | 10/2013 |
| WO | 2013166588 | 11/2013 |
| WO | 2014031899 | 2/2014 |
| WO | 2014194439 | 12/2014 |
| WO | 2016090605 | 6/2016 |
| WO | 2018081013 | 5/2018 |
| WO | 2018102562 | 6/2018 |
| WO | 2018129531 | 7/2018 |
| WO | 2019056579 | 3/2019 |
| WO | 2019089613 | 5/2019 |
| WO | WO-2022161730 A1 * | 8/2022 .......... G02C 13/005 |
| WO | 2022204031 | 9/2022 |
| WO | 2022204674 | 9/2022 |

OTHER PUBLICATIONS

Search machine translation of JP-2017-194301-A to Toshio et al., Face Shape Measuring Device and Method, translated Nov. 25, 2023, 24 pages. (Year: 2023).*

Method and Apparatus for Determining a Fit of a Visual Equipment, certified copy of priority document EP 21305107.1 to Andoche et al. of WO 2022/161730 A1, Jan. 28, 2021 [retrieved Nov. 25, 2023], 53 pages. (Year: 2021).*

Habermann et al., ReTiCaM: Real-time Human Performance Capture from Monocular Video, author/ publicly uploaded: Jan. 23, 2019 [retrieved Nov. 25, 2023], 17 pages. Retrieved: 'https://www.researchgate.net/publication/328137039_ReTiCaM_Real-time_Human_Performance_Capture_from_Monocular_Video (Year: 2019).*

U.S. Appl. No. 17/208,159, filed Mar. 22, 2021, True Size Eyewear in Real Time.

"U.S. Appl. No. 17/208,159, Non Final Office Action mailed May 3, 2022", 14 pgs.

"International Application Serial No. PCT/US2022/021151, International Search Report mailed Jun. 28, 2022", 5 pgs.

"International Application Serial No. PCT/US2022/021151, Written Opinion mailed Jun. 28, 2022", 8 pgs.

"International Application Serial No. PCT/US2022/071250, Invitation to Pay Additional Fees mailed Jul. 8, 2022", 19 pgs.

Hassner, Tal, "Effective Face Frontalization in Unconstrained Images", 2015 IEEE Conference on Computer Vision and Pattern Recognition (CVPR), IEEE, (Jun. 7, 2015), 10 pgs.

"U.S. Appl. No. 17/208,159, Response filed Aug. 3, 2022 to Non Final Office Action mailed May 3, 2022", 8 pgs.

"International Application Serial No. PCT/US2022/071250, International Search Report mailed Aug. 30, 2022", 7 pgs.

"International Application Serial No. PCT/US2022/071250, Written Opinion mailed Aug. 30, 2022", 18 pgs.

"U.S. Appl. No. 17/208,159, Notice of Allowance mailed Sep. 27, 2022", 7 pgs.

"U.S. Appl. No. 17/208,159, Corrected Notice of Allowability mailed Dec. 20, 2022", 33 pgs.

(56) References Cited

OTHER PUBLICATIONS

"International Application Serial No. PCT/US2022/021151, International Preliminary Report on Patentability mailed Oct. 5, 2023", 10 pgs.

"International Application Serial No. PCT/US2022/071250, International Preliminary Report on Patentability mailed Oct. 5, 2023", 20 pgs.

* cited by examiner

US 12,067,804 B2

TRUE SIZE EYEWEAR EXPERIENCE IN REAL TIME

TECHNICAL FIELD

The present disclosure relates generally to providing augmented reality experiences using a messaging application.

BACKGROUND

Augmented-Reality (AR) is a modification of a virtual environment. For example, in Virtual Reality (VR), a user is completely immersed in a virtual world, whereas in AR, the user is immersed in a world where virtual objects are combined or superimposed on the real world. An AR system aims to generate and present virtual objects that interact realistically with a real-world environment and with each other. Examples of AR applications can include single or multiple player video games, instant messaging systems, and the like.

BRIEF DESCRIPTION OF THE SEVERAL VIEWS OF THE DRAWINGS

In the drawings, which are not necessarily drawn to scale, like numerals may describe similar components in different views. To easily identify the discussion of any particular element or act, the most significant digit or digits in a reference number refer to the figure number in which that element is first introduced. Some nonlimiting examples are illustrated in the figures of the accompanying drawings in which.

DETAILED DESCRIPTION

Figure 1:
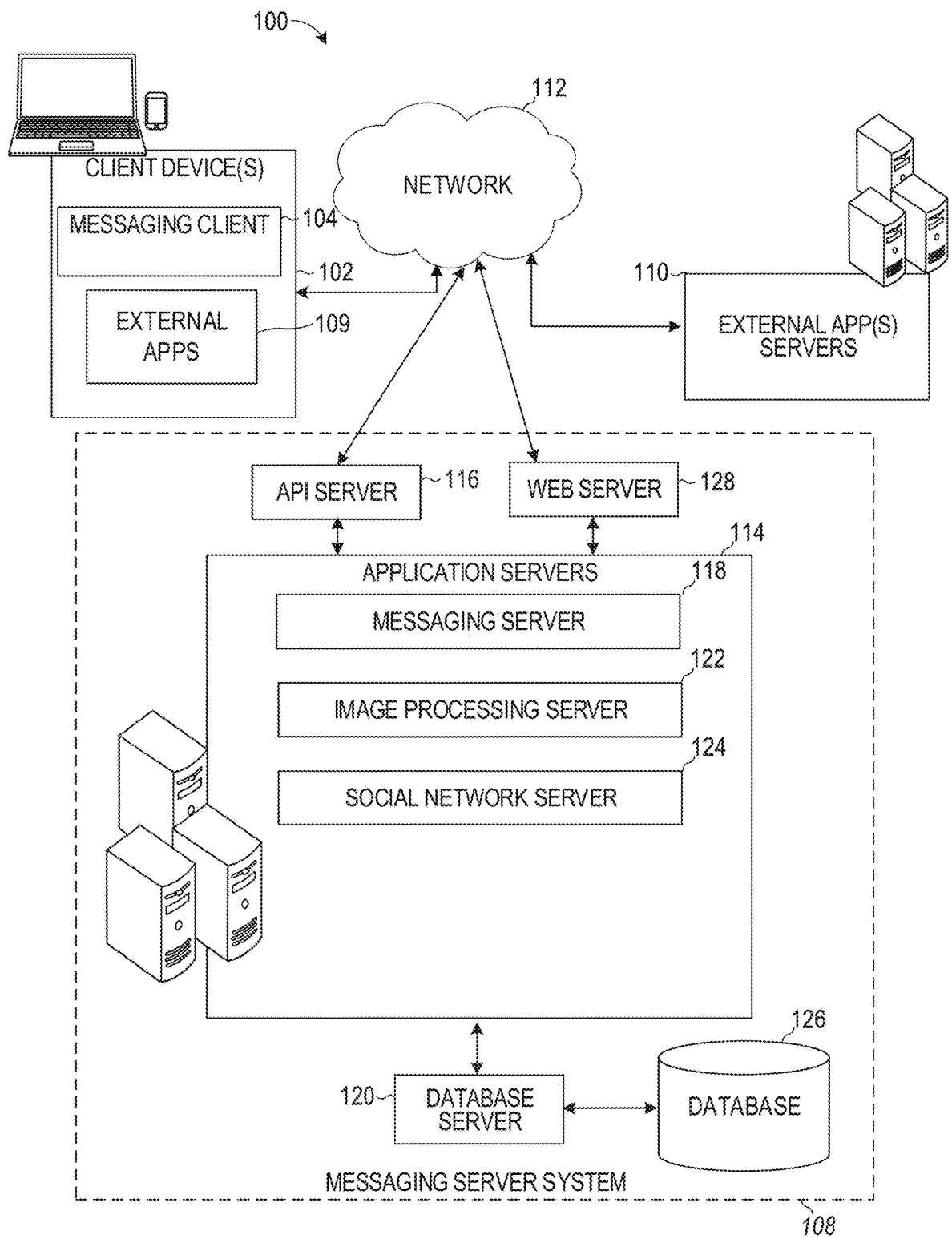
FIG. 1 is a diagrammatic representation of a networked environment in which the present disclosure may be deployed, in accordance with some examples.

The description that follows includes systems, methods, techniques, instruction sequences, and computing machine program products that embody illustrative examples of the disclosure. In the following description, for the purposes of explanation, numerous specific details are set forth in order to provide an understanding of various examples. It will be evident, however, to those skilled in the art, that examples may be practiced without these specific details. In general, well-known instruction instances, protocols, structures, and techniques are not necessarily shown in detail.

Typically, virtual reality (VR) and augmented reality (AR) systems allow users to add augmented reality elements, such as augmented reality glasses, to a face of the user depicted in a captured image. To do so, the typical VR/AR systems use specialized techniques that require calibration to determine a scale of the user's face in the image. For example, such systems instruct the user to place a reference object, such as a credit card, on the user's face or next to the user's face so that a scale of the face can be computed. The systems can then display augmented reality glasses on the user's face based on the calibration. While such systems generally work well, the need to calibrate the systems places an additional burden on the users and takes away from the enjoyment of the experience. Also, computing the scale by calibrating the system takes additional time and resources, making such systems less efficient for general applications.

The disclosed techniques improve the efficiency of using an electronic device which implements or otherwise accesses an AR/VR system by computing a true or real-world scale of a user's face by combining a select set of facial landmarks with a depth map of the user's face. Specifically, the disclosed techniques receive an image that includes a depiction of a face of a user and generate a plurality of facial landmarks based on the received image. Facial landmarks (or landmarks on the face) can correspond to a predefined region of a person's face such as a nose, mouth, eyes, etc. The disclosed techniques remove a set of interfering facial landmarks from the plurality of facial landmarks resulting in a remaining set of landmarks of the plurality of landmarks. The disclosed techniques obtain a depth map for the face of the user and compute a real-world scale of the face of the user based on the depth map and the remaining set of landmarks. The real-world scale of the face is then used to adjust a size of an augmented reality element, such as augmented reality glasses (e.g., eyewear) or an augmented reality hat. The real-world scale together with a facial topology is also used to identify the appropriate position over which to add or display the augmented reality element on the user's face. As the user moves the face around in a video, the positioning of the augmented reality element continues to be changed to remain fixed to the identified position of the face. The real-world scale of the face continues to be updated as new images of a video depicting the user's face are received and processed in a similar manner.

In this way, the disclosed techniques can apply one or more visual effects to the user's face in the current image without performing any calibration operations or pre-capture operations. This improves the overall experience of the user in using the electronic device and reduces the overall amount of system resources needed to accomplish a task.

Networked Computing Environment

FIG. 1 is a block diagram showing an example messaging system 100 for exchanging data (e.g., messages and associated content) over a network. The messaging system 100 includes multiple instances of a client device 102, each of which hosts a number of applications, including a messaging client 104 and other external applications 109 (e.g., third-party applications). Each messaging client 104 is communicatively coupled to other instances of the messaging client 104 (e.g., hosted on respective other client devices 102), a messaging server system 108 and external app(s) servers 110 via a network 112 (e.g., the Internet). A messaging client 104 can also communicate with locally-hosted third-party applications 109 using Applications Program Interfaces (APIs).

A messaging client 104 is able to communicate and exchange data with other messaging clients 104 and with the messaging server system 108 via the network 112. The data exchanged between messaging clients 104, and between a messaging client 104 and the messaging server system 108, includes functions (e.g., commands to invoke functions) as well as payload data (e.g., text, audio, video or other multimedia data).

The messaging server system 108 provides server-side functionality via the network 112 to a particular messaging client 104. While certain functions of the messaging system 100 are described herein as being performed by either a messaging client 104 or by the messaging server system 108, the location of certain functionality either within the messaging client 104 or the messaging server system 108 may be a design choice. For example, it may be technically preferable to initially deploy certain technology and functionality within the messaging server system 108 but to later migrate this technology and functionality to the messaging client 104 where a client device 102 has sufficient processing capacity.

The messaging server system 108 supports various services and operations that are provided to the messaging client 104. Such operations include transmitting data to, receiving data from, and processing data generated by the messaging client 104. This data may include message content, client device information, geolocation information, media augmentation and overlays, message content persistence conditions, social network information, and live event information, as examples. Data exchanges within the messaging system 100 are invoked and controlled through functions available via user interfaces (UIs) of the messaging client 104.

Turning now specifically to the messaging server system 108, an Application Program Interface (API) server 116 is coupled to, and provides a programmatic interface to, application servers 114. The application servers 114 are communicatively coupled to a database server 120, which facilitates access to a database 126 that stores data associated with messages processed by the application servers 114. Similarly, a web server 128 is coupled to the application servers 114, and provides web-based interfaces to the application servers 114. To this end, the web server 128 processes incoming network requests over the Hypertext Transfer Protocol (HTTP) and several other related protocols.

The Application Program Interface (API) server 116 receives and transmits message data (e.g., commands and message payloads) between the client device 102 and the application servers 114. Specifically, the Application Program Interface (API) server 116 provides a set of interfaces (e.g., routines and protocols) that can be called or queried by the messaging client 104 in order to invoke functionality of the application servers 114. The Application Program Interface (API) server 116 exposes various functions supported by the application servers 114, including account registration, login functionality, the sending of messages, via the application servers 114, from a particular messaging client 104 to another messaging client 104, the sending of media files (e.g., images or video) from a messaging client 104 to a messaging server 118, and for possible access by another messaging client 104, the settings of a collection of media data (e.g., story), the retrieval of a list of friends of a user of a client device 102, the retrieval of such collections, the retrieval of messages and content, the addition and deletion of entities (e.g., friends) to an entity graph (e.g., a social graph), the location of friends within a social graph, and opening an application event (e.g., relating to the messaging client 104).

The application servers 114 host a number of server applications and subsystems, including for example a messaging server 118, an image processing server 122, and a social network server 124. The messaging server 118 implements a number of message processing technologies and functions, particularly related to the aggregation and other processing of content (e.g., textual and multimedia content) included in messages received from multiple instances of the messaging client 104. As will be described in further detail, the text and media content from multiple sources may be aggregated into collections of content (e.g., called stories or galleries). These collections are then made available to the messaging client 104. Other processor- and memory-intensive processing of data may also be performed server-side by the messaging server 118, in view of the hardware requirements for such processing.

The application servers 114 also include an image processing server 122 that is dedicated to performing various image processing operations, typically with respect to images or video within the payload of a message sent from or received at the messaging server 118.

Image processing server 122 is used to implement scan functionality of the augmentation system 208. Scan functionality includes activating and providing one or more augmented reality experiences on a client device 102 when an image is captured by the client device 102. Specifically, the messaging client 104 on the client device 102 can be used to activate a camera. The camera displays one or more real-time images or a video to a user along with one or more icons or identifiers of one or more augmented reality experiences. The user can select a given one of the identifiers to launch the corresponding augmented reality experience or perform a desired image modification (e.g., adding augmented reality eyewear or a hat to a face depicted in an image).

Figure 3:
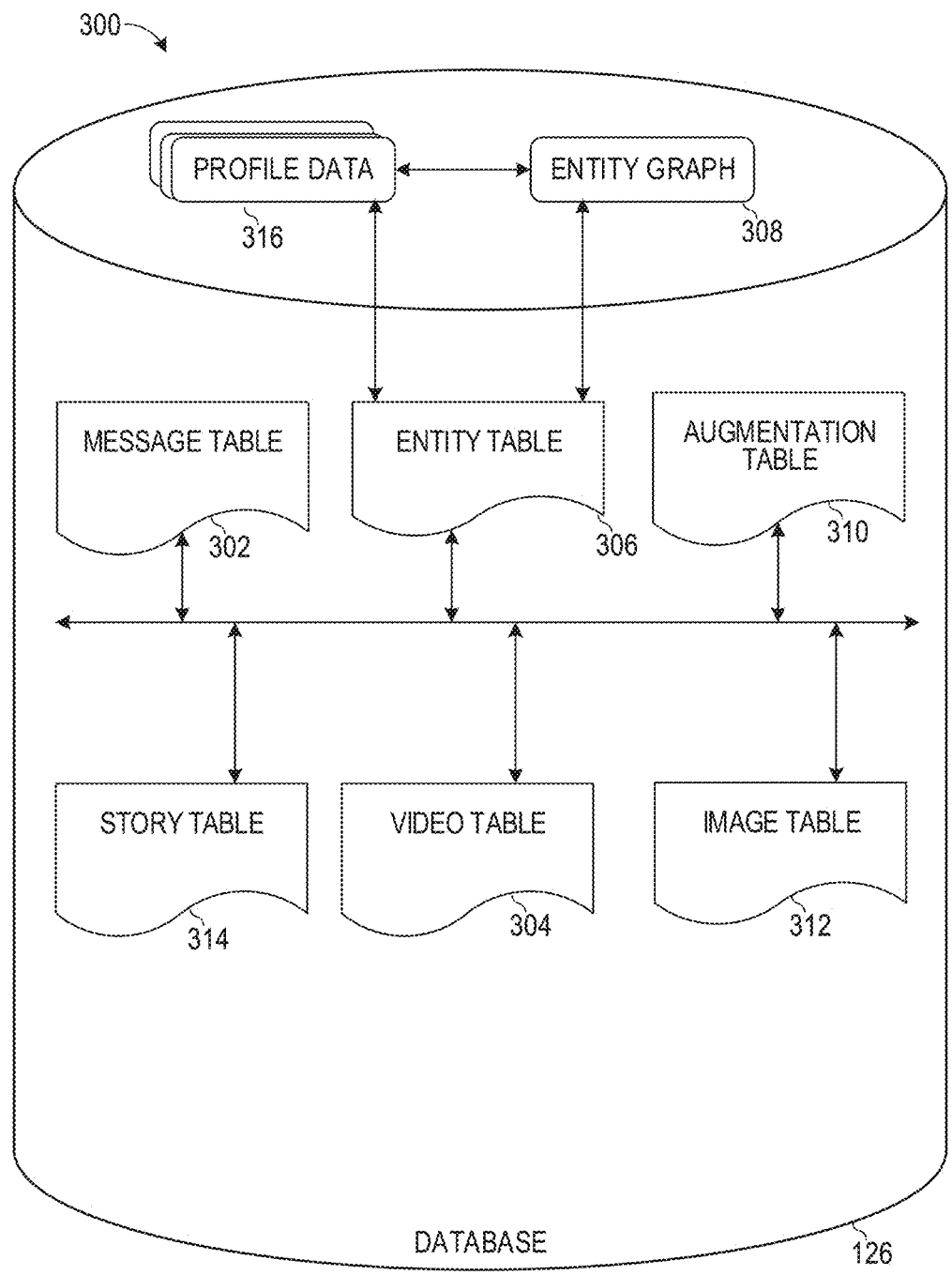
FIG. 3 is a diagrammatic representation of a data structure as maintained in a database, in accordance with some examples.

The social network server 124 supports various social networking functions and services and makes these functions and services available to the messaging server 118. To this end, the social network server 124 maintains and accesses an entity graph 308 (as shown in FIG. 3) within the database 126. Examples of functions and services supported by the social network server 124 include the identification of other users of the messaging system 100 with which a particular user has relationships or is "following," and also the identification of other entities and interests of a particular user.

Returning to the messaging client 104, features and functions of an external resource (e.g., a third-party application 109 or applet) are made available to a user via an interface of the messaging client 104. The messaging client 104 receives a user selection of an option to launch or access features of an external resource (e.g., a third-party resource), such as external apps 109. The external resource may be a third-party application (external apps 109) installed on the client device 102 (e.g., a "native app"), or a small-scale version of the third-party application (e.g., an "applet") that is hosted on the client device 102 or remote of the client device 102 (e.g., on third-party servers 110). The small-scale version of the third-party application includes a subset of features and functions of the third-party application (e.g., the full-scale, native version of the third-party standalone application) and is implemented using a markup-language document. In one example, the small-scale version of the third-party application (e.g., an "applet") is a web-based, markup-language version of the third-party application and is embedded in the messaging client 104. In addition to using markup-language documents (e.g., a .*ml file), an applet may incorporate a scripting language (e.g., a .*js file or a .json file) and a style sheet (e.g., a .*ss file).

In response to receiving a user selection of the option to launch or access features of the external resource (external app 109), the messaging client 104 determines whether the selected external resource is a web-based external resource or a locally-installed external application. In some cases, external applications 109 that are locally installed on the client device 102 can be launched independently of and separately from the messaging client 104, such as by selecting an icon, corresponding to the external application 109, on a home screen of the client device 102. Small-scale versions of such external applications can be launched or accessed via the messaging client 104 and, in some examples, no or limited portions of the small-scale external application can be accessed outside of the messaging client 104. The small-scale external application can be launched by the messaging client 104 receiving, from a external app(s) server 110, a markup-language document associated with the small-scale external application and processing such a document.

In response to determining that the external resource is a locally-installed external application 109, the messaging client 104 instructs the client device 102 to launch the external application 109 by executing locally-stored code corresponding to the external application 109. In response to determining that the external resource is a web-based resource, the messaging client 104 communicates with the external app(s) servers 110 to obtain a markup-language document corresponding to the selected resource. The messaging client 104 then processes the obtained markup-language document to present the web-based external resource within a user interface of the messaging client 104.

The messaging client 104 can notify a user of the client device 102, or other users related to such a user (e.g., "friends"), of activity taking place in one or more external resources. For example, the messaging client 104 can provide participants in a conversation (e.g., a chat session) in the messaging client 104 with notifications relating to the current or recent use of an external resource by one or more members of a group of users. One or more users can be invited to join in an active external resource or to launch a recently-used but currently inactive (in the group of friends) external resource. The external resource can provide participants in a conversation, each using a respective messaging client messaging clients 104, with the ability to share an item, status, state, or location in an external resource with one or more members of a group of users into a chat session. The shared item may be an interactive chat card with which members of the chat can interact, for example, to launch the corresponding external resource, view specific information within the external resource, or take the member of the chat to a specific location or state within the external resource. Within a given external resource, response messages can be sent to users on the messaging client 104. The external resource can selectively include different media items in the responses, based on a current context of the external resource.

The messaging client 104 can present a list of the available external resources (e.g., third-party or external applications 109 or applets) to a user to launch or access a given external resource. This list can be presented in a context-sensitive menu. For example, the icons representing different ones of the external application 109 (or applets) can vary based on how the menu is launched by the user (e.g., from a conversation interface or from a non-conversation interface).

System Architecture

Figure 2:
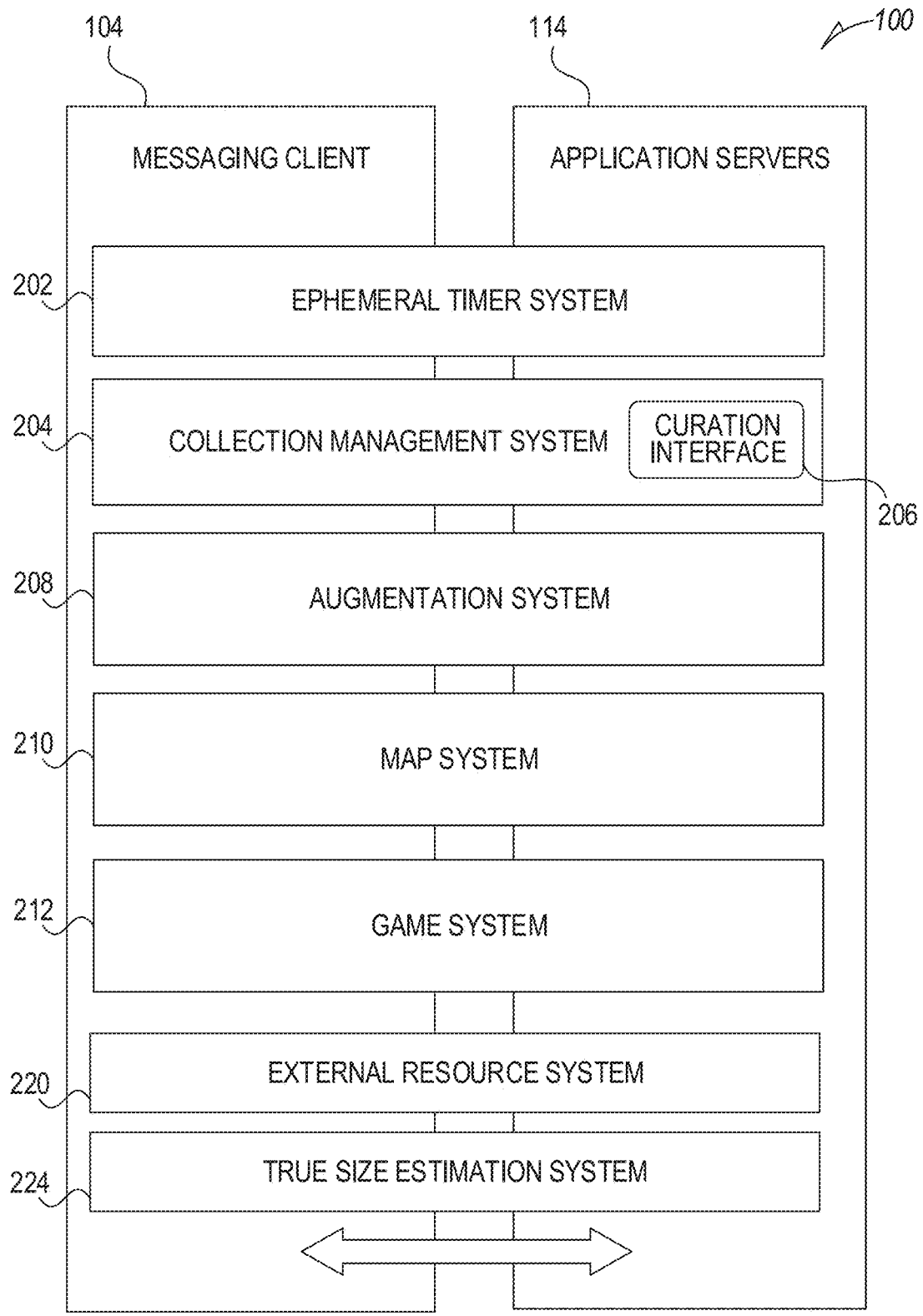
FIG. 2 is a diagrammatic representation of a messaging client application, in accordance with some examples.

FIG. 2 is a block diagram illustrating further details regarding the messaging system 100, according to some examples. Specifically, the messaging system 100 is shown to comprise the messaging client 104 and the application servers 114. The messaging system 100 embodies a number of subsystems, which are supported on the client side by the messaging client 104 and on the sever side by the application servers 114. These subsystems include, for example, an ephemeral timer system 202, a collection management system 204, an augmentation system 208, a map system 210, a game system 212, and an external resource system 220.

The ephemeral timer system 202 is responsible for enforcing the temporary or time-limited access to content by the messaging client 104 and the messaging server 118. The ephemeral timer system 202 incorporates a number of timers that, based on duration and display parameters associated with a message, or collection of messages (e.g., a story), selectively enable access (e.g., for presentation and display) to messages and associated content via the messaging client 104. Further details regarding the operation of the ephemeral timer system 202 are provided below.

The collection management system 204 is responsible for managing sets or collections of media (e.g., collections of text, image video, and audio data). A collection of content (e.g., messages, including images, video, text, and audio) may be organized into an "event gallery" or an "event story." Such a collection may be made available for a specified time period, such as the duration of an event to which the content relates. For example, content relating to a music concert may be made available as a "story" for the duration of that music concert. The collection management system 204 may also be responsible for publishing an icon that provides notification of the existence of a particular collection to the user interface of the messaging client 104.

The collection management system 204 furthermore includes a curation interface 206 that allows a collection manager to manage and curate a particular collection of content. For example, the curation interface 206 enables an event organizer to curate a collection of content relating to a specific event (e.g., delete inappropriate content or redundant messages). Additionally, the collection management system 204 employs machine vision (or image recognition technology) and content rules to automatically curate a content collection. In certain examples, compensation may be paid to a user for the inclusion of user-generated content into a collection. In such cases, the collection management system 204 operates to automatically make payments to such users for the use of their content.

The augmentation system 208 provides various functions that enable a user to augment (e.g., annotate or otherwise modify or edit) media content associated with a message. For example, the augmentation system 208 provides functions related to the generation and publishing of media overlays for messages processed by the messaging system 100. The augmentation system 208 operatively supplies a media overlay or augmentation (e.g., an image filter) to the messaging client 104 based on a geolocation of the client device 102. In another example, the augmentation system 208 operatively supplies a media overlay to the messaging client 104 based on other information, such as social network information of the user of the client device 102. A media overlay may include audio and visual content and visual effects. Examples of audio and visual content include pictures, texts, logos, animations, and sound effects. An example of a visual effect includes color overlaying. The audio and visual content or the visual effects can be applied to a media content item (e.g., a photo) at the client device 102. For example, the media overlay may include text, a graphical element, or image that can be overlaid on top of a photograph taken by the client device 102. In another example, the media overlay includes an identification of a location overlay (e.g., Venice beach), a name of a live event, or a name of a merchant overlay (e.g., Beach Coffee House). In another example, the augmentation system 208 uses the geolocation of the client device 102 to identify a media overlay that includes the name of a merchant at the geolocation of the client device 102. The media overlay may include other indicia associated with the merchant. The media overlays may be stored in the database 126 and accessed through the database server 120.

In some examples, the augmentation system 208 provides a user-based publication platform that enables users to select a geolocation on a map and upload content associated with the selected geolocation. The user may also specify circumstances under which a particular media overlay should be offered to other users. The augmentation system 208 generates a media overlay that includes the uploaded content and associates the uploaded content with the selected geolocation.

In other examples, the augmentation system 208 provides a merchant-based publication platform that enables merchants to select a particular media overlay associated with a geolocation via a bidding process. For example, the augmentation system 208 associates the media overlay of the highest bidding merchant with a corresponding geolocation for a predefined amount of time. The augmentation system 208 communicates with the image processing server 122 to obtain augmented reality experiences and presents identifiers of such experiences in one or more user interfaces (e.g., as icons over a real-time image or video or as thumbnails or icons in interfaces dedicated for presented identifiers of augmented reality experiences). Once an augmented reality experience is selected, one or more images, videos, or augmented reality graphical elements are retrieved and presented as an overlay on top of the images or video captured by the client device 102. In some cases, the camera is switched to a front-facing view (e.g., the front-facing camera of the client device 102 is activated in response to activation of a particular augmented reality experience) and the images from the front-facing camera of the client device 102 start being displayed on the client device 102 instead of the rear-facing camera of the client device 102. The one or more images, videos, or augmented reality graphical elements are retrieved and presented as an overlay on top of the images that are captured and displayed by the front-facing camera of the client device 102.

In other examples, the augmentation system 208 is able to communicate and exchange data with another augmentation system 208 on another client device 102 and with the server via the network 106. The data exchanged can include a session identifier that identifies the shared AR session, a transformation between a first client device 102 and a second client device 102 (e.g., a plurality of client devices 102 include the first and second devices) that is used to align the shared AR session to a common point of origin, a common coordinate frame, functions (e.g., commands to invoke functions) as well as other payload data (e.g., text, audio, video or other multimedia data).

The augmentation system 208 sends the transformation to the second client device 102 so that the second client device 102 can adjust the AR coordinate system based on the transformation. In this way, the first and second client devices 102 synch up their coordinate systems and frames for displaying content in the AR session. Specifically, the augmentation system 208 computes the point of origin of the second client device 102 in the coordinate system of the first client device 102. The augmentation system 208 can then determine an offset in the coordinate system of the second client device 102 based on the position of the point of origin from the perspective of the second client device 102 in the coordinate system of the second client device 102. This offset is used to generate the transformation so that the second client device 102 generates AR content in according to a common coordinate system or frame as the first client device 102.

The augmentation system 208 that can communicate with the client device 102 to establish individual or shared AR sessions. The augmentation system 208 can also be coupled to the messaging server 118 to establish an electronic group communication session (e.g., group chat, instant messaging) for the client devices 102 in a shared AR session. The electronic group communication session can be associated with a session identifier provided by the client devices 102 to gain access to the electronic group communication session and to the shared AR session. In one example, the client devices 102 first gain access to the electronic group communication session and then obtain the session identifier in the electronic group communication session that allows the client devices 102 to access to the shared AR session. In some examples, the client devices 102 are able to access the shared AR session without aid or communication with the augmentation system 208 in the application servers 114.

The map system 210 provides various geographic location functions, and supports the presentation of map-based media content and messages by the messaging client 104. For example, the map system 210 enables the display of user icons or avatars (e.g., stored in profile data 316) on a map to indicate a current or past location of "friends" of a user, as well as media content (e.g., collections of messages including photographs and videos) generated by such friends, within the context of a map. For example, a message posted by a user to the messaging system 100 from a specific geographic location may be displayed within the context of a map at that particular location to "friends" of a specific user on a map interface of the messaging client 104. A user can furthermore share his or her location and status information (e.g., using an appropriate status avatar) with other users of the messaging system 100 via the messaging client 104, with this location and status information being similarly displayed within the context of a map interface of the messaging client 104 to selected users.

The game system 212 provides various gaming functions within the context of the messaging client 104. The messaging client 104 provides a game interface providing a list of available games (e.g., web-based games or web-based applications) that can be launched by a user within the context of the messaging client 104, and played with other users of the messaging system 100. The messaging system 100 further enables a particular user to invite other users to participate in the play of a specific game, by issuing invitations to such other users from the messaging client 104. The messaging client 104 also supports both voice and text messaging (e.g., chats) within the context of gameplay, provides a leaderboard for the games, and also supports the provision of in-game rewards (e.g., coins and items).

The external resource system 220 provides an interface for the messaging client 104 to communicate with external app(s) servers 110 to launch or access external resources. Each external resource (apps) server 110 hosts, for example, a markup language (e.g., HTML5) based application or small-scale version of an external application (e.g., game, utility, payment, or ride-sharing application that is external to the messaging client 104). The messaging client 104 may launch a web-based resource (e.g., application) by accessing the HTML5 file from the external resource (apps) servers 110 associated with the web-based resource. In certain examples, applications hosted by external resource servers 110 are programmed in JavaScript leveraging a Software Development Kit (SDK) provided by the messaging server 118. The SDK includes Application Programming Interfaces (APIs) with functions that can be called or invoked by the web-based application. In certain examples, the messaging server 118 includes a JavaScript library that provides a given third-party resource access to certain user data of the messaging client 104. HTML5 is used as an example technology for programming games, but applications and resources programmed based on other technologies can be used.

In order to integrate the functions of the SDK into the web-based resource, the SDK is downloaded by an external resource (apps) server 110 from the messaging server 118 or is otherwise received by the external resource (apps) server 110. Once downloaded or received, the SDK is included as part of the application code of a web-based external resource. The code of the web-based resource can then call or invoke certain functions of the SDK to integrate features of the messaging client 104 into the web-based resource.

The SDK stored on the messaging server 118 effectively provides the bridge between an external resource (e.g., third-party or external applications 109 or applets and the messaging client 104). This provides the user with a seamless experience of communicating with other users on the messaging client 104, while also preserving the look and feel of the messaging client 104. To bridge communications between an external resource and a messaging client 104, in certain examples, the SDK facilitates communication between external resource servers 110 and the messaging client 104. In certain examples, a WebViewJavaScriptBridge running on a client device 102 establishes two one-way communication channels between a external resource and the messaging client 104. Messages are sent between the external resource and the messaging client 104 via these communication channels asynchronously. Each SDK function invocation is sent as a message and callback. Each SDK function is implemented by constructing a unique callback identifier and sending a message with that callback identifier.

By using the SDK, not all information from the messaging client 104 is shared with external resource servers 110. The SDK limits which information is shared based on the needs of the external resource. In certain examples, each external resource server 110 provides an HTML5 file corresponding to the web-based external resource to the messaging server 118. The messaging server 118 can add a visual representation (such as a box art or other graphic) of the web-based external resource in the messaging client 104. Once the user selects the visual representation or instructs the messaging client 104 through a GUI of the messaging client 104 to access features of the web-based external resource, the messaging client 104 obtains the HTML5 file and instantiates the resources necessary to access the features of the web-based external resource.

The messaging client 104 presents a graphical user interface (e.g., a landing page or title screen) for an external resource. During, before, or after presenting the landing page or title screen, the messaging client 104 determines whether the launched external resource has been previously authorized to access user data of the messaging client 104. In response to determining that the launched external resource has been previously authorized to access user data of the messaging client 104, the messaging client 104 presents another graphical user interface of the external resource that includes functions and features of the external resource. In response to determining that the launched external resource has not been previously authorized to access user data of the messaging client 104, after a threshold period of time (e.g., 3 seconds) of displaying the landing page or title screen of the external resource, the messaging client 104 slides up (e.g., animates a menu as surfacing from a bottom of the screen to a middle of or other portion of the screen) a menu for authorizing the external resource to access the user data. The menu identifies the type of user data that the external resource will be authorized to use. In response to receiving a user selection of an accept option, the messaging client 104 adds the external resource to a list of authorized external resources and allows the external resource to access user data from the messaging client 104. In some examples, the external resource is authorized by the messaging client 104 to access the user data in accordance with an OAuth 2 framework.

The messaging client 104 controls the type of user data that is shared with external resources based on the type of external resource being authorized. For example, external resources that include full-scale external applications (e.g., a third-party or external application 109) are provided with access to a first type of user data (e.g., only two-dimensional avatars of users with or without different avatar characteristics). As another example, external resources that include small-scale versions of external applications (e.g., web-based versions of third-party applications) are provided with access to a second type of user data (e.g., payment information, two-dimensional avatars of users, three-dimensional avatars of users, and avatars with various avatar characteristics). Avatar characteristics include different ways to customize a look and feel of an avatar, such as different poses, facial features, clothing, and so forth.

The true size estimation system 224 computes a real-world scale of a user's face that is depicted in an image, such as based on facial landmarks (or subset of facial landmarks) and data received from a depth sensor. For example, the true size estimation system 224 can perform object recognition on the captured video feed to generate a plurality of landmarks of the face depicted in a received image. In response to generating the plurality of landmarks, the true size estimation system 224 removes a set of interfering landmarks from the plurality of landmarks resulting in a remaining set of landmarks of the plurality of landmarks, such as by removing a hair landmark or chin landmark. In some cases, the true size estimation system 224 removes landmarks that have a visibility parameter or stability parameter that is lower than a specified value. In some cases, the true size estimation system 224 sorts the landmarks based on respective visibility and stability parameters to generate the remaining set of landmarks. The true size estimation system 224 obtains a depth map and then computes a real-word scale of the face of the user based on the depth map and the remaining set of landmarks. An illustrative implementation of the true size estimation system 224 is shown and described in connection with FIG. 5 below.

Specifically, the true size estimation system 224 is a component that can be accessed by an AR/VR application implemented on the client device 102. The AR/VR application uses an RGB camera to capture a monocular image of a user's real-world face. The AR/VR application applies various trained machine learning techniques on the captured image of the face and obtains a depth map and to apply one or more visual effects to the captured image. In some implementations, the AR/VR application continuously captures images of the user's face in real time or periodically to continuously or periodically update the applied one or more visual effects (e.g., the augmented reality eyewear or hat). This allows the user to move around in the real world and see the one or more visual effects update in real time.

Data Architecture

FIG. 3 is a schematic diagram illustrating data structures 300, which may be stored in the database 126 of the messaging server system 108, according to certain examples. While the content of the database 126 is shown to comprise a number of tables, it will be appreciated that the data could be stored in other types of data structures (e.g., as an object-oriented database).

The database 126 includes message data stored within a message table 302. This message data includes, for any particular one message, at least message sender data, message recipient (or receiver) data, and a payload. Further details regarding information that may be included in a message, and included within the message data stored in the message table 302, is described below with reference to FIG. 4.

An entity table 306 stores entity data, and is linked (e.g., referentially) to an entity graph 308 and profile data 316. Entities for which records are maintained within the entity table 306 may include individuals, corporate entities, organizations, objects, places, events, and so forth. Regardless of entity type, any entity regarding which the messaging server system 108 stores data may be a recognized entity. Each entity is provided with a unique identifier, as well as an entity type identifier (not shown).

The entity graph 308 stores information regarding relationships and associations between entities. Such relationships may be social, professional (e.g., work at a common corporation or organization) interested-based or activity-based, merely for example.

The profile data 316 stores multiple types of profile data about a particular entity. The profile data 316 may be selectively used and presented to other users of the messaging system 100, based on privacy settings specified by a particular entity. Where the entity is an individual, the profile data 316 includes, for example, a user name, telephone number, address, settings (e.g., notification and privacy settings), as well as a user-selected avatar representation (or collection of such avatar representations). A particular user may then selectively include one or more of these avatar representations within the content of messages communicated via the messaging system 100, and on map interfaces displayed by messaging clients 104 to other users. The collection of avatar representations may include "status avatars," which present a graphical representation of a status or activity that the user may select to communicate at a particular time.

Where the entity is a group, the profile data 316 for the group may similarly include one or more avatar representations associated with the group, in addition to the group name, members, and various settings (e.g., notifications) for the relevant group.

The database 126 also stores augmentation data, such as overlays or filters, in an augmentation table 310. The augmentation data is associated with and applied to videos (for which data is stored in a video table 304) and images (for which data is stored in an image table 312).

The database 126 can also store data pertaining to individual and shared AR sessions. This data can include data communicated between an AR session client controller of a first client device 102 and another AR session client controller of a second client device 102, and data communicated between the AR session client controller and the augmentation system 208. Data can include data used to establish the common coordinate frame of the shared AR scene, the transformation between the devices, the session identifier, images depicting a body, skeletal joint positions, wrist joint positions, feet, and so forth.

Filters, in one example, are overlays that are displayed as overlaid on an image or video during presentation to a recipient user. Filters may be of various types, including user-selected filters from a set of filters presented to a sending user by the messaging client 104 when the sending user is composing a message. Other types of filters include geolocation filters (also known as geo-filters), which may be presented to a sending user based on geographic location. For example, geolocation filters specific to a neighborhood or special location may be presented within a user interface by the messaging client 104, based on geolocation information determined by a Global Positioning System (GPS) unit of the client device 102.

Another type of filter is a data filter, which may be selectively presented to a sending user by the messaging client 104, based on other inputs or information gathered by the client device 102 during the message creation process. Examples of data filters include current temperature at a specific location, a current speed at which a sending user is traveling, battery life for a client device 102, or the current time.

Other augmentation data that may be stored within the image table 312 includes augmented reality content items (e.g., corresponding to applying augmented reality experiences). An augmented reality content item or augmented reality item may be a real-time special effect and sound that may be added to an image or a video.

As described above, augmentation data includes augmented reality content items, overlays, image transformations, AR images, and similar terms that refer to modifications that may be applied to image data (e.g., videos or images). This includes real-time modifications, which modify an image as it is captured using device sensors (e.g., one or multiple cameras) of a client device 102 and then displayed on a screen of the client device 102 with the modifications. This also includes modifications to stored content, such as video clips in a gallery that may be modified. For example, in a client device 102 with access to multiple augmented reality content items, a user can use a single video clip with multiple augmented reality content items to see how the different augmented reality content items will modify the stored clip. For example, multiple augmented reality content items that apply different pseudorandom movement models can be applied to the same content by selecting different augmented reality content items for the content. Similarly, real-time video capture may be used with an illustrated modification to show how video images currently being captured by sensors of a client device 102 would modify the captured data. Such data may simply be displayed on the screen and not stored in memory, or the content captured by the device sensors may be recorded and stored in memory with or without the modifications (or both). In some systems, a preview feature can show how different augmented reality content items will look within different windows in a display at the same time. This can, for example, enable multiple windows with different pseudo-random animations to be viewed on a display at the same time.

Data and various systems using augmented reality content items or other such transform systems to modify content using this data can thus involve detection of objects (e.g., faces, hands, bodies, cats, dogs, surfaces, objects, etc.), tracking of such objects as they leave, enter, and move around the field of view in video frames, and the modification or transformation of such objects as they are tracked. In various examples, different methods for achieving such transformations may be used. Some examples may involve generating a three-dimensional mesh model of the object or objects, and using transformations and animated textures of the model within the video to achieve the transformation. In other examples, tracking of points on an object may be used to place an image or texture (which may be two dimensional or three dimensional) at the tracked position. In still further examples, neural network analysis of video frames may be used to place images, models, or textures in content (e.g., images or frames of video). Augmented reality content items thus refer both to the images, models, and textures used to create transformations in content, as well as to additional modeling and analysis information needed to achieve such transformations with object detection, tracking, and placement.

Real-time video processing can be performed with any kind of video data (e.g., video streams, video files, etc.) saved in a memory of a computerized system of any kind. For example, a user can load video files and save them in a memory of a device, or can generate a video stream using sensors of the device. Additionally, any objects can be processed using a computer animation model, such as a human's face and parts of a human body, animals, or non-living things such as chairs, cars, or other objects.

In some examples, when a particular modification is selected along with content to be transformed, elements to be transformed are identified by the computing device, and then detected and tracked if they are present in the frames of the video. The elements of the object are modified according to the request for modification, thus transforming the frames of the video stream. Transformation of frames of a video stream can be performed by different methods for different kinds of transformation. For example, for transformations of frames mostly referring to changing forms of object's elements, characteristic points for each element of an object are calculated (e.g., using an Active Shape Model (ASM) or other known methods). Then, a mesh based on the characteristic points is generated for each of the at least one element of the object. This mesh is used in the following stage of tracking the elements of the object in the video stream. In the process of tracking, the mentioned mesh for each element is aligned with a position of each element. Then, additional points are generated on the mesh. A first set of first points is generated for each element based on a request for modification, and a set of second points is generated for each element based on the set of first points and the request for modification. Then, the frames of the video stream can be transformed by modifying the elements of the object on the basis of the sets of first and second points and the mesh. In such method, a background of the modified object can be changed or distorted as well by tracking and modifying the background.

In some examples, transformations changing some areas of an object using its elements can be performed by calculating characteristic points for each element of an object and generating a mesh based on the calculated characteristic points. Points are generated on the mesh, and then various areas based on the points are generated. The elements of the object are then tracked by aligning the area for each element with a position for each of the at least one element, and properties of the areas can be modified based on the request for modification, thus transforming the frames of the video stream. Depending on the specific request for modification, properties of the mentioned areas can be transformed in different ways. Such modifications may involve changing color of areas; removing at least some part of areas from the frames of the video stream; including one or more new objects into areas which are based on a request for modification; and modifying or distorting the elements of an area or object. In various examples, any combination of such modifications or other similar modifications may be used. For certain models to be animated, some characteristic points can be selected as control points to be used in determining the entire state-space of options for the model animation.

In some examples of a computer animation model to transform image data using face detection, the face is detected on an image with use of a specific face detection algorithm (e.g., Viola-Jones). Then, an Active Shape Model (ASM) algorithm is applied to the face region of an image to detect facial feature reference points.

Other methods and algorithms suitable for face detection can be used. For example, in some examples, features are located using a landmark, which represents a distinguishable point present in most of the images under consideration. For facial landmarks, for example, the location of the left eye pupil may be used. If an initial landmark is not identifiable (e.g., if a person has an eyepatch), secondary landmarks may be used. Such landmark identification procedures may be used for any such objects. In some examples, a set of landmarks forms a shape. Shapes can be represented as vectors using the coordinates of the points in the shape. One shape is aligned to another with a similarity transform (allowing translation, scaling, and rotation) that minimizes the average Euclidean distance between shape points. The mean shape is the mean of the aligned training shapes.

In some examples, a search for landmarks from the mean shape aligned to the position and size of the face determined by a global face detector is started. Such a search then repeats the steps of suggesting a tentative shape by adjusting the locations of shape points by template matching of the image texture around each point and then conforming the tentative shape to a global shape model until convergence occurs. In some systems, individual template matches are unreliable, and the shape model pools the results of the weak template matches to form a stronger overall classifier. The entire search is repeated at each level in an image pyramid, from coarse to fine resolution.

A transformation system can capture an image or video stream on a client device (e.g., the client device 102) and perform complex image manipulations locally on the client device 102 while maintaining a suitable user experience, computation time, and power consumption. The complex image manipulations may include size and shape changes, emotion transfers (e.g., changing a face from a frown to a smile), state transfers (e.g., aging a subject, reducing apparent age, changing gender), style transfers, graphical element application, and any other suitable image or video manipulation implemented by a convolutional neural network that has been configured to execute efficiently on the client device 102.

In some examples, a computer animation model to transform image data can be used by a system where a user may capture an image or video stream of the user (e.g., a selfie) using a client device 102 having a neural network operating as part of a messaging client 104 operating on the client device 102. The transformation system operating within the messaging client 104 determines the presence of a face within the image or video stream and provides modification icons associated with a computer animation model to transform image data, or the computer animation model can be present as associated with an interface described herein. The modification icons include changes that may be the basis for modifying the user's face within the image or video stream as part of the modification operation. Once a modification icon is selected, the transformation system initiates a process to convert the image of the user to reflect the selected modification icon (e.g., generate a smiling face on the user). A modified image or video stream may be presented in a graphical user interface displayed on the client device 102 as soon as the image or video stream is captured, and a specified modification is selected. The transformation system may implement a complex convolutional neural network on a portion of the image or video stream to generate and apply the selected modification. That is, the user may capture the image or video stream and be presented with a modified result in real-time or near real-time once a modification icon has been selected. Further, the modification may be persistent while the video stream is being captured, and the selected modification icon remains toggled. Machine-taught neural networks may be used to enable such modifications.

The graphical user interface, presenting the modification performed by the transformation system, may supply the user with additional interaction options. Such options may be based on the interface used to initiate the content capture and selection of a particular computer animation model (e.g., initiation from a content creator user interface). In various examples, a modification may be persistent after an initial selection of a modification icon. The user may toggle the modification on or off by tapping or otherwise selecting the face being modified by the transformation system and store it for later viewing or browse to other areas of the imaging application. Where multiple faces are modified by the transformation system, the user may toggle the modification on or off globally by tapping or selecting a single face modified and displayed within a graphical user interface. In some examples, individual faces, among a group of multiple faces, may be individually modified, or such modifications may be individually toggled by tapping or selecting the individual face or a series of individual faces displayed within the graphical user interface.

A story table 314 stores data regarding collections of messages and associated image, video, or audio data, which are compiled into a collection (e.g., a story or a gallery). The creation of a particular collection may be initiated by a particular user (e.g., each user for which a record is maintained in the entity table 306). A user may create a "personal story" in the form of a collection of content that has been created and sent/broadcast by that user. To this end, the user interface of the messaging client 104 may include an icon that is user-selectable to enable a sending user to add specific content to his or her personal story.

A collection may also constitute a "live story," which is a collection of content from multiple users that is created manually, automatically, or using a combination of manual and automatic techniques. For example, a "live story" may constitute a curated stream of user-submitted content from various locations and events. Users whose client devices have location services enabled and are at a common location event at a particular time may, for example, be presented with an option, via a user interface of the messaging client 104, to contribute content to a particular live story. The live story may be identified to the user by the messaging client 104, based on his or her location. The end result is a "live story" told from a community perspective.

A further type of content collection is known as a "location story," which enables a user whose client device 102 is located within a specific geographic location (e.g., on a college or university campus) to contribute to a particular collection. In some examples, a contribution to a location story may require a second degree of authentication to verify that the end user belongs to a specific organization or other entity (e.g., is a student on the university campus).

As mentioned above, the video table 304 stores video data that, in one example, is associated with messages for which records are maintained within the message table 302. Similarly, the image table 312 stores image data associated with messages for which message data is stored in the entity table 306. The entity table 306 may associate various augmentations from the augmentation table 310 with various images and videos stored in the image table 312 and the video table 304.

Data Communications Architecture

Figure 4:
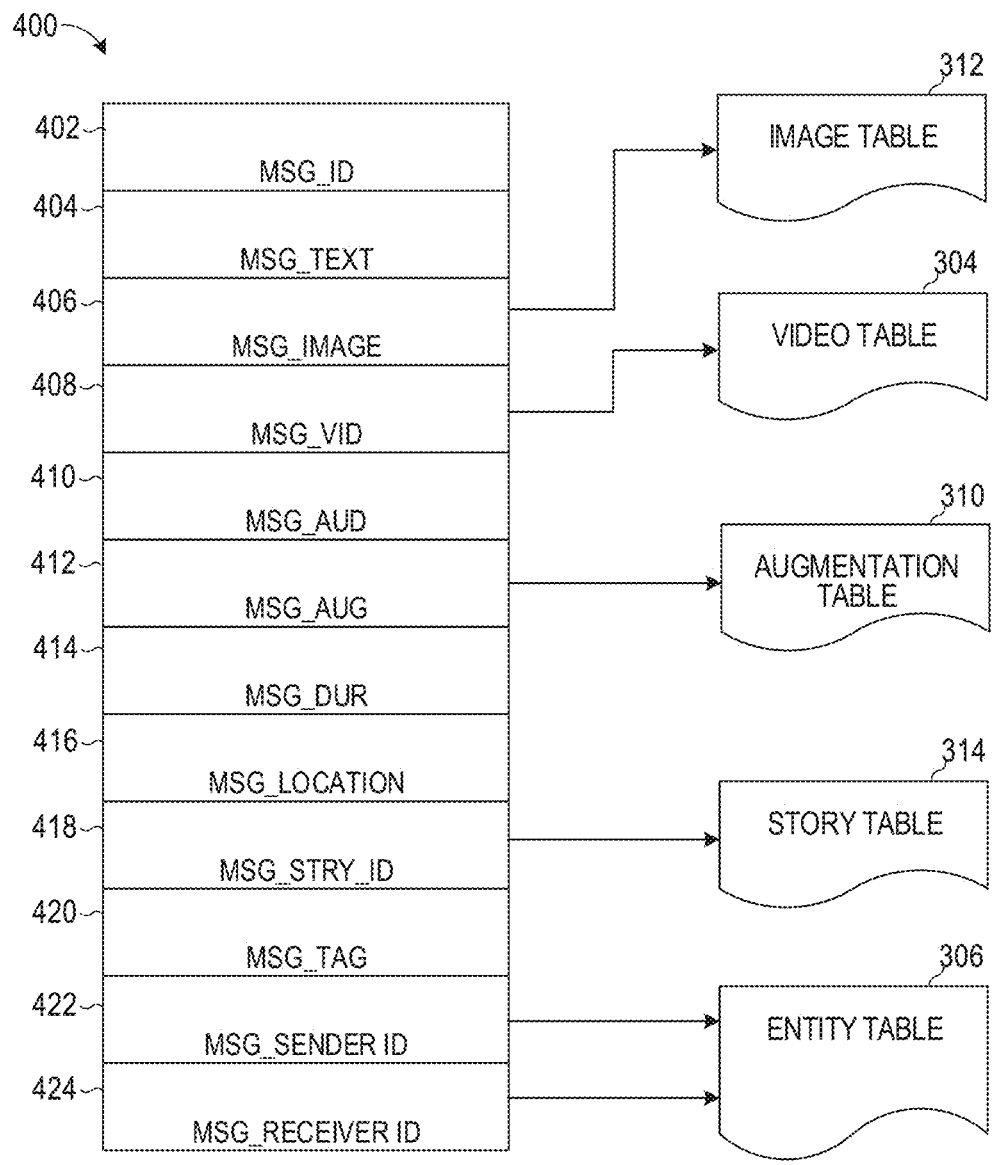
FIG. 4 is a diagrammatic representation of a message, in accordance with some examples.

FIG. 4 is a schematic diagram illustrating a structure of a message 400, according to some examples, generated by a messaging client 104 for communication to a further messaging client 104 or the messaging server 118. The content of a particular message 400 is used to populate the message table 302 stored within the database 126, accessible by the messaging server 118. Similarly, the content of a message 400 is stored in memory as "in-transit" or "in-flight" data of the client device 102 or the application servers 114. A message 400 is shown to include the following example components:

- message identifier 402: a unique identifier that identifies the message 400.
- message text payload 404: text, to be generated by a user via a user interface of the client device 102, and that is included in the message 400.
- message image payload 406: image data, captured by a camera component of a client device 102 or retrieved from a memory component of a client device 102, and that is included in the message 400. Image data for a sent or received message 400 may be stored in the image table 312.
- message video payload 408: video data, captured by a camera component or retrieved from a memory component of the client device 102, and that is included in the message 400. Video data for a sent or received message 400 may be stored in the video table 304.
- message audio payload 410: audio data, captured by a microphone or retrieved from a memory component of the client device 102, and that is included in the message 400.
- message augmentation data 412: augmentation data (e.g., filters, stickers, or other annotations or enhancements) that represents augmentations to be applied to message image payload 406, message video payload 408, or message audio payload 410 of the message 400. Augmentation data for a sent or received message 400 may be stored in the augmentation table 310.

message duration parameter 414: parameter value indicating, in seconds, the amount of time for which content of the message (e.g., the message image payload 406, message video payload 408, message audio payload 410) is to be presented or made accessible to a user via the messaging client 104.

message geolocation parameter 416: geolocation data (e.g., latitudinal and longitudinal coordinates) associated with the content payload of the message. Multiple message geolocation parameter 416 values may be included in the payload, each of these parameter values being associated with respect to content items included in the content (e.g., a specific image within the message image payload 406, or a specific video in the message video payload 408).

message story identifier 418: identifier values identifying one or more content collections (e.g., "stories" identified in the story table 314) with which a particular content item in the message image payload 406 of the message 400 is associated. For example, multiple images within the message image payload 406 may each be associated with multiple content collections using identifier values.

message tag 420: each message 400 may be tagged with multiple tags, each of which is indicative of the subject matter of content included in the message payload. For example, where a particular image included in the message image payload 406 depicts an animal (e.g., a lion), a tag value may be included within the message tag 420 that is indicative of the relevant animal. Tag values may be generated manually, based on user input, or may be automatically generated using, for example, image recognition.

message sender identifier 422: an identifier (e.g., a messaging system identifier, email address, or device identifier) indicative of a user of the client device 102 on which the message 400 was generated and from which the message 400 was sent.

message receiver identifier 424: an identifier (e.g., a messaging system identifier, email address, or device identifier) indicative of a user of the client device 102 to which the message 400 is addressed.

The contents (e.g., values) of the various components of message 400 may be pointers to locations in tables within which content data values are stored. For example, an image value in the message image payload 406 may be a pointer to (or address of) a location within an image table 312. Similarly, values within the message video payload 408 may point to data stored within a video table 304, values stored within the message augmentation data 412 may point to data stored in an augmentation table 310, values stored within the message story identifier 418 may point to data stored in a story table 314, and values stored within the message sender identifier 422 and the message receiver identifier 424 may point to user records stored within an entity table 306.

True Size Estimation System

Figure 5:
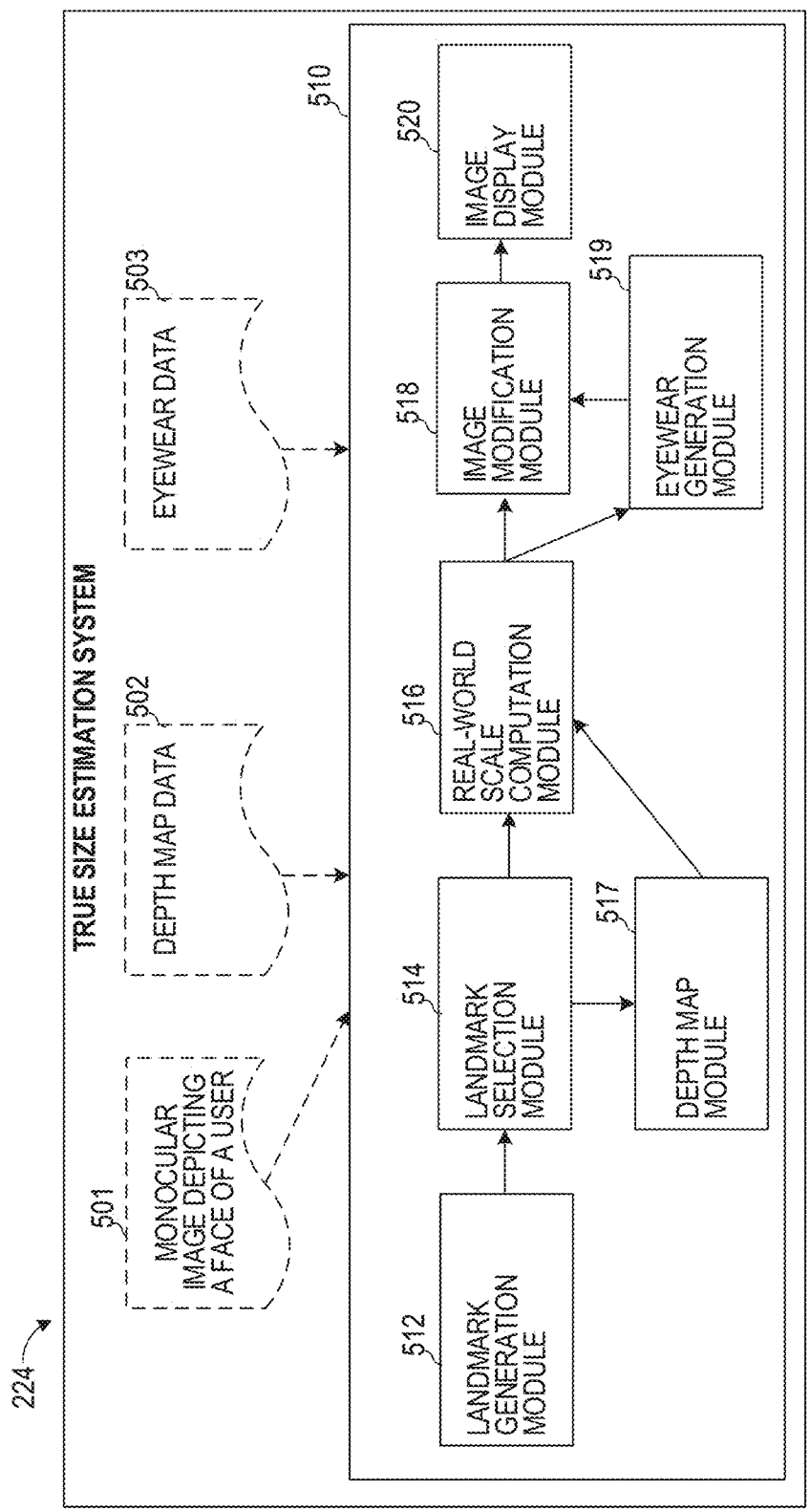
FIG. 5 is a block diagram showing an example true size estimation system, according to example examples.

FIG. 5 is a block diagram showing an example true size estimation system 224, according to example examples. True size estimation system 224 includes a set of components 510 that operate on a set of input data (e.g., a monocular image depicting a face of a user 501, depth map data 502, and eyewear data 503). True size estimation system 224 includes a landmark generation module 512, a landmark selection module 514, a depth map module 517, a real-world scale computation module 516, an image modification module 518, an eyewear generation module 519, and an image display module 520. All or some of the components of the true size estimation system 224 can be implemented by a server, in which case, the monocular image depicting a face of the user 501 and the depth map data 502 are provided to the server by the client device 102. In some cases, some or all of the components of the true size estimation system 224 can be implemented by the client device 102.

Figure 6:
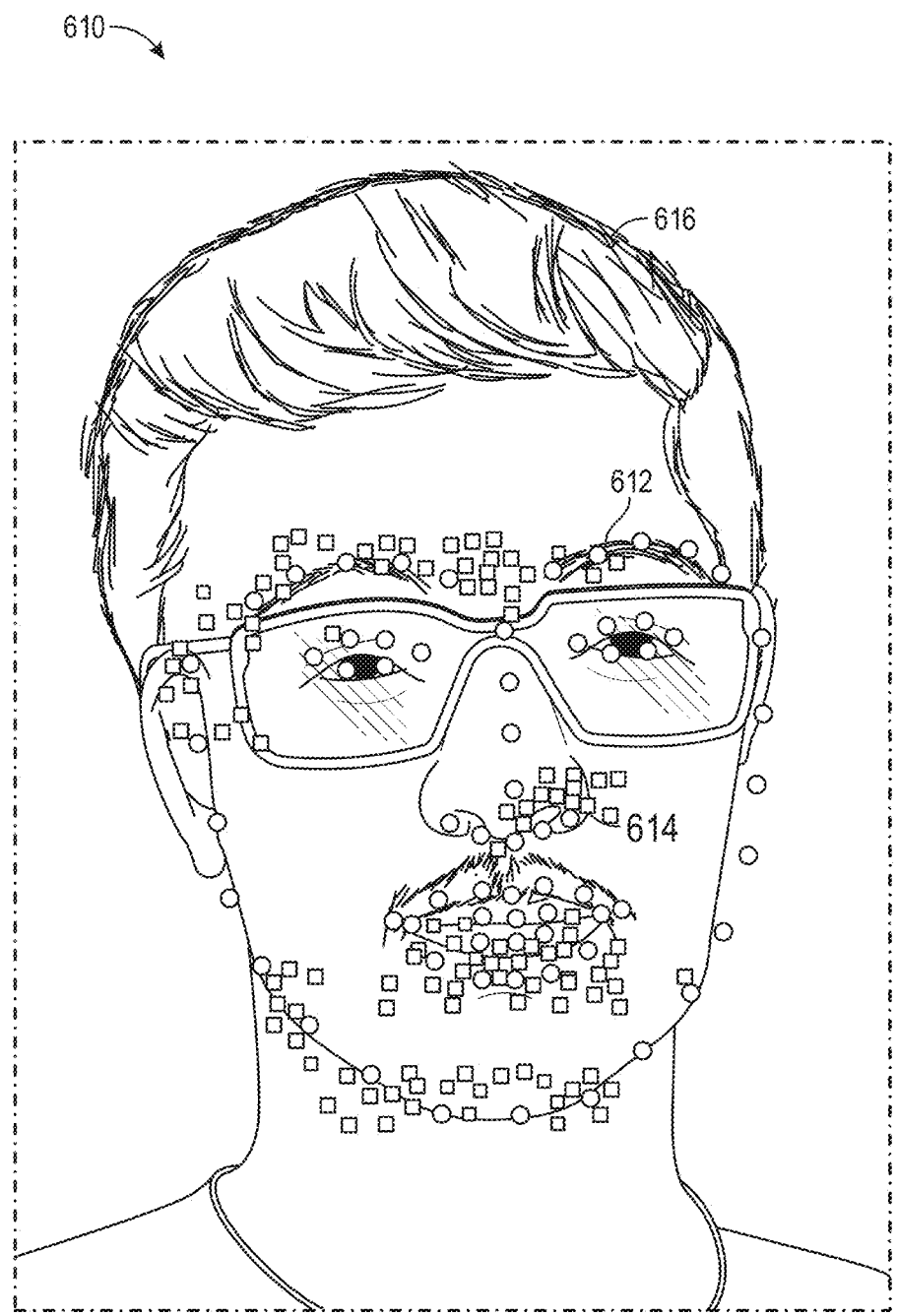
FIGS. 6-9 are diagrammatic representations of outputs of the true size estimation system, in accordance with some examples.

The landmark generation module 512 receives a monocular image depicting a face of a user 501. This image can be received as part of a real-time video stream, a previously captured video stream or a new image captured by a camera of the client device 102. The landmark generation module 512 applies one or more machine learning techniques to identify and segment a face of the user from the background of the monocular image depicting the face of the user 501. The landmark generation module 512 can then apply one or more machine learning techniques to identify one or more landmarks on the identified face. For example, as shown in FIG. 6, the landmark generation module 512 can generate an output image 610 in which a plurality of landmarks 616, 612 and 614 are provided. Each landmark uniquely and specifically identifies a region of the face, such as the eyebrows, the eyes, the nose, temple, the nose bridge, the mouth, the nose, the ears, the hair, the cheeks, the forehead, and so forth.

The landmark generation module 512 can compute visibility and stability parameters for each of the identified landmarks. The visibility parameter specifies a score, rank or amount of the given landmark that is visible in the monocular image depicting a face of a user 501. In an example, the landmark generation module 512 computes the visibility parameter by retrieving a generic three-dimensional (3D) facial model representation. The landmark generation module 512 identifies a set of landmarks on the 3D facial model representation. The landmark generation module 512 selects a given landmark from the identified landmarks of the user's face and matches the given landmark to a corresponding landmark on the 3D facial model. For example, the landmark generation module 512 selects the ears landmark and matches the ears landmark to the ears portion of the 3D facial model. The landmark generation module 512 computes how much of the ears landmark matches the ears portion of the 3D facial model to determine a level of visibility or visibility parameter. In an implementation, if 60 percent of the ears landmark matches the ears portion, the visibility parameter is set to a score of 60 percent. Namely, the visibility parameter is proportional to the amount of overlap or amount by which the landmark matches the corresponding portion of the 3D facial model.

The landmark generation module 512 continues to compute the visibility parameter for the rest of the landmarks that are identified in the received image in a similar way using the 3D facial model. After obtaining the visibility parameter for each of the landmarks identified in the face, the landmark generation module 512 determines the visibility parameter of each landmark as a function of a number of the remaining set of landmarks that match the generic 3D facial model representation. Specifically, the landmark generation module 512 computes how many of the landmarks have a visibility score that is greater than a certain threshold value (e.g., greater than 75 percent). The landmark generation module 512 then computes an overall visibility parameter for the identified landmarks based on the number of landmarks that have the visibility score that is greater than the threshold value. The greater the number of landmarks with the visibility score greater than the threshold value, the greater the overall visibility parameter.

The landmark generation module 512 can also compute a stability parameter for each of the identified landmarks. The stability parameter indicates how much each given landmark moves over a threshold number of frames. For example, the landmark generation module 512 can receive a sequence of frames of a video that include the monocular image depicting a face of a user 501. After identifying the landmarks on the face, the landmark generation module 512 can determine the 3D or 2D positions of the landmarks in the image. The landmark generation module 512 detects changes to the 3D or 2D positions of each landmark. Based on the amount of movement or changes to the 3D or 2D positions, the landmark generation module 512 generates and computes a corresponding stability parameter for the given landmark. Landmarks that have less amount of movement are assigned a greater stability parameter score than those that are determined to move more than a threshold amount per threshold number of frames (e.g., over 40 frames).

In some cases, the landmark generation module 512 computes the stability parameter of each of the landmarks based on a frame rate associated with the client device 102 used to capture the video that depicts the face of the user. Namely, a client device 102 that has a first frame rate can be associated with a greater number of frames over which the stability parameter is computed than another client device with a lower second frame rate. Namely, the threshold number of frames can vary based on the frame rate of the client device 102. After computing the stability and visibility parameters of each of the landmarks, the landmark generation module 512 sorts and ranks the landmarks based on their respective stability and visibility parameters.

In some cases, prior to performing the visibility and stability parameter computations, the landmark generation module 512 can remove a set of interfering landmarks from the identified set of landmarks of the face. Namely, the landmark generation module 512 can access a predetermined list of known or predetermined set of interfering landmarks (e.g., a hair region, a facial garment (e.g., a face mask or eyeglasses), a neck region). In response to determining that one of the identified landmarks corresponds or is included among the predetermined set of interfering landmarks, the landmark generation module 512 can remove or discard or not consider such an identified landmark. After removing the set of interfering landmarks from the plurality of landmarks, the landmark generation module 512 provides a resulting set of remaining landmarks of the total identified plurality of landmarks to the landmark selection module 514. In some cases, the removal of the interfering landmarks can be performed after computing the visibility and stability parameters of all of the identified plurality of landmarks on the face and before the top landmarks are selected. This way, even though a given landmark (e.g., a facial garment) is associated with a highest visibility and stability parameter than all other landmarks (e.g., the eyes and nose), the given landmark is not included or selected among the top landmarks by the landmark selection module 514 because it is considered to be an interfering landmark.

The landmark generation module 512 provides the identified landmarks and their respective visibility and stability parameters to the landmark selection module 514. The landmark selection module 514 selects a set of top landmarks that are associated with a greater visibility and greater stability parameters than a remaining set of landmarks. In some cases, the landmark selection module 514 can receive an indication of an augmented reality element that is to be included in the image that depicts the user's face. Based on the type of augmented reality element (e.g., eyewear augmented reality element), the landmark generation module 512 obtains a threshold quantity or number of landmarks that are to be selected as the top landmarks. For example, if the eyewear augmented reality element is selected, the threshold number of top landmarks includes two top landmarks that need to be selected. In this case, the landmark selection module 514 obtains and tracks the two landmarks that are ranked higher than all other landmarks that are identified based on their respective visibility and stability parameters (or metrics). The threshold number of top landmarks can also be specified by the user.

In some implementations, the landmark selection module 514 selects the top landmarks at random. For example, for a first sequence of frames or a first duration of a video, the landmark selection module 514 can selects a first set of landmarks (e.g., eyes and nose) that have visibility and stability parameters that exceed a specified value. Then, for a second sequence of frames or a second duration of the video, the landmark selection module 514 can selects a second set of landmarks (e.g., eyes and ears) that have visibility and stability parameters that exceed the specified value. Namely, the landmark selection module 514 can identify a collection of landmarks (e.g., more than the threshold number of top landmarks) which have visibility and stability parameters that are greater than a specified value or that satisfy a criterion or criteria. The landmark selection module 514 can then alternate and vary randomly which subset of the collection of landmarks (e.g., which two of the multiple collection of landmarks) to include in the threshold number of top landmarks.

In an implementation, based on tracking the two landmarks, the landmark selection module 514 can provide the information pertaining to the two landmarks to the real-world scale computation module 516 to compute the real-world scale of the user depicted in the image. In this way, the real-world scale computation module 516 can compute a real-world scale of a user in a video or image based on a first set of landmarks at a first point in time (e.g., during a first portion of a video) and can compute the real-world scale of the user in the video or image based on a different second set of landmarks at a second point in time. The operations for identifying the facial landmarks, removing certain landmarks, and computing the stability and visibility parameters of the facial landmarks are repeated for each video frame or each subset of video frames to update the stability and visibility parameters. The updated stability and visibility parameters are provided to the landmark selection module 514 to update the landmarks selected as the top landmarks and iteratively correct the real-world scale of the face based on the updated plurality of landmarks.

The depth map module 517 receives depth map data 502 from a depth sensor or depth camera of the client device 102. The depth map data 502 is associated with the image or video being processed by the landmark generation module 512 and the landmark selection module 514. The depth map module 517 receives a face segmentation mask for the face depicted in the monocular image depicting the face of the user 501, such as from the landmark generation module 512. The depth map module 517 applies momentum smoothing to the depth map data 502 based on the face segmentation mask. The depth map module 517 provides the smoothed depth map to the real-world scale computation module 516. The real-world scale computation module 516 computes the real-world scale of the user's face depicted in the image based on the top landmarks provided by the landmark selection module 514 and the smoothed depth map received from the depth map module 517. For example, the real-world scale computation module 516 can determine a distance to a given landmark from the client device 102 based on the smoothed depth map. Based on the distance, the real-world scale computation module 516 can compute the real-world facial measurements of the landmarks identified in the image received from the client device 102. Namely, the real-world scale computation module 516 can use heuristics or machine learning techniques to compute the real-world physical size and measurements of the user's face when a landmark appears at a certain size and is at a certain distance away from the client device 102. Using this information, the real-world scale computation module 516 can determine a scale that transforms the real-world physical measurements to the sizes of the landmarks and face depicted in the image captured by the client device 102.

The real-world scale computation module 516 provides the scale to the image modification module 518 and the eyewear generation module 519. The eyewear generation module 519 obtains an augmented reality graphical element that includes augmented reality eyewear. In an example, the real-world scale computation module 516 receives eyewear data 503. The eyewear data 503 defines the physical material and rigid properties of physical sunglasses or eyeglasses. The eyewear data 503 also includes the physical measurements of the physical sunglasses or eyeglasses. The eyewear data 503 also provides an augmented reality element having a size and dimensions and behavior (deformation properties) that represents the physical sunglasses or eyeglasses. The eyewear data 503 can include information from a physical glasses designer that specifies physical attributes of the glasses, such as physical measurements, a style of the physical glasses, a lens shape and color, and a frame style and color.

The eyewear generation module 519 can increase or decrease a size of the augmented reality element based on the real-world scale of the user's face provided by the real-world scale computation module 516. For example, if the user's face in the image is at a first distance to the client device 102, the scale can be determined based on the landmarks and smoothed depth data to be a first value. The eyewear generation module 519, in this case, adjusts the size of the augmented reality element based on the first value. If the user's face is moved further away from the client device 102, the face becomes smaller and is at a farther second distance. In this case, the scale can be determined to be a second smaller value than the first. In this case, the eyewear generation module 519 reduces the size of the augmented reality element based on the second value to be smaller.

The eyewear generation module 519 provides the augmented reality element having the adjusted scale to the image modification module 518. The image modification module 518 positions the scaled augmented reality element on the face of the user depicted in the image or video. In some cases, the image modification module 518 identifies a nose bridge landmark based on the output of the landmark generation module 512. The image modification module 518 then identifies a nose bridge portion of the augmented reality element and centers the nose bridge portion of the augmented reality element on top of the nose bridge landmark. In some implementations, the image modification module 518 identifies a start point and end point of the nose bridge landmark. The image modification module 518 selects a point between the start and end points of the nose bridge landmark over which to position the nose bridge portion of the augmented reality element. The point between the start and end points can be heuristically determined, set by a user, or learned by a machine learning technique. In some cases, the image modification module 518 initially places the augmented reality element at a midpoint between the start and end points. For example, the image modification module 518 can determine a topology of the face of the user based on the landmarks generated by the landmark generation module 512. The image modification module 518 can then position the scaled augmented reality graphical element within the image or video based on the topology of the user's face. In an example, the image modification module 518 positions a nose bridge portion of the augmented reality graphical element a predetermined distance above a nose bridge landmark within the topology.

Figure 7:
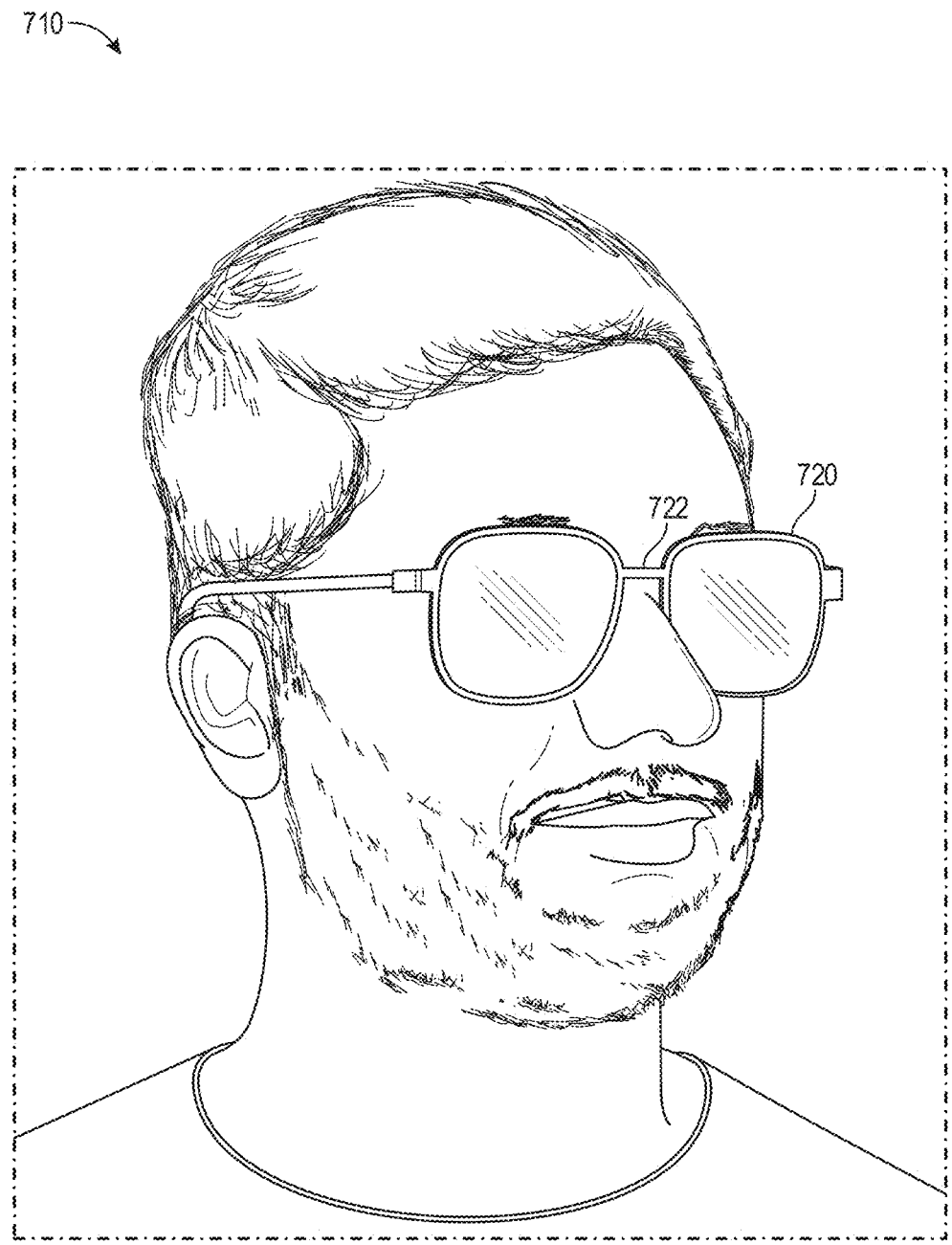

For example, as shown in FIG. 7, the image modification module 518 places the augmented reality eyewear 720 on the image 710 depicting the user's face. The nose bridge portion 722 of the augmented reality eyewear 720 is placed and positioned over the nose bridge landmark of the user's face.

The image modification module 518 can detect a user's finger in the video stream received from the client device. The image modification module 518 can determine that the user's finger overlaps the nose bridge portion of the augmented reality element. The image modification module 518 can determine then that the finger is moved vertically towards the eyebrows. In response, the image modification module 518 adjusts the point at which the augmented reality element is positioned on the nose bridge portion by a specified amount to be closer to the eyebrows depending on the amount of movement of the finger. The image modification module 518 can determine then that the finger is moved vertically towards the mouth. In response, the image modification module 518 adjusts the point at which the augmented reality element is positioned on the nose bridge portion by a specified amount to be further from the eyebrows and closer to the mouth depending on the amount of movement of the finger. The image modification module 518 can record or store the position along the nose bridge landmark over which the nose bridge portion is placed. The image modification module 518 can place subsequent or other eyewear augmented reality elements such that their respective nose bridge portions are positioned at the stored position on the nose bridge landmark.

The image modification module 518 can adjust the image captured by the camera and based on the output of the eyewear generation module 519. The image modification module 518 adjusts the way in which the augmented reality eyeglasses or hat is positioned on a user(s) depicted in an image. Image display module 520 combines the adjustments made by the image modification module 518 into the received monocular image depicting the user's face. The image is provided by the image display module 520 to the client device 102 and can then be sent to another user or stored for later access and display.

In an example, the eyewear generation module 519 can recommend or automatically select an augmented reality eyewear element to display on the user's face based on fit factors computed for a plurality of augmented reality eyewear elements. For example, the eyewear generation module 519 can receive, as part of the eyewear data 503, a plurality of physical measurements of a plurality of physical glasses. The physical glasses can be associated with a particular manufacturer or can be a specified set of popular glasses or can include all of the physical glasses that have associated eyewear data 503. The eyewear generation module 519 can select a subset of physical glasses for which to compute the fit factor based on a style and one or more attributes associated with the user, such as an age of the user, a gender of the user, preferences of the user, and the computed real-world scale of the face. Namely, the eyewear generation module 519 can determine that the physical size of the user's face is of a specified value and can select a subset of physical glasses that match the specified value. In another example, the eyewear generation module 519 can determine that the user in the image is a child and can select a set of child friendly glasses for which to compute the fit factor.

The eyewear generation module 519 computes a fit factor for each of the physical glasses based on the physical measurements of the glasses provided by the eyewear data 503 and the real-world scale of the face of the user. In an implementation, the eyewear generation module 519 computes a fit factor for each of the glasses by determining a first distance between a nose bridge portion of each one of the plurality of physical glasses and a temples portion of the respective one of the plurality of physical glasses.

The eyewear generation module 519 computes a second distance in the computed real-world scale of the face of the user between a nose bridge and a cheek bone or temple of the face of the user. Namely, the eyewear generation module 519 determines the real-world physical measurements of the landmarks depicted in the image of the user's face and the smoothed depth map and computes the distance between the nose bridge landmark and a cheek bone or temple landmark of the physical measurements of the face of the user. The eyewear generation module 519 then computes the fit factor for each of the glasses as a function of the first distance and the second distance. In an example, the fit factor represents a difference between the first and second distances, such that a smaller fit factor represents a better fit for the user. In some cases, the value for the fit factor is inversely related to the difference between the first and second distances, such that a greater fit factor represents a better fit for the user. Namely, the eyewear generation module 519 computes the fit factor for a given one of the glasses based on how close the distance between nose bridge portion of the given glasses and a temples portion of the given glasses is to the distance between the nose bridge landmark and a cheek bone or temple landmark of the user's face. The eyewear generation module 519 ranks and sorts all of the physical glasses based on the computed fit factor and automatically selects one or a subset of the physical glasses having a top fit factor (e.g., a fit factor better than the rest) to present to the user.

Figure 8:
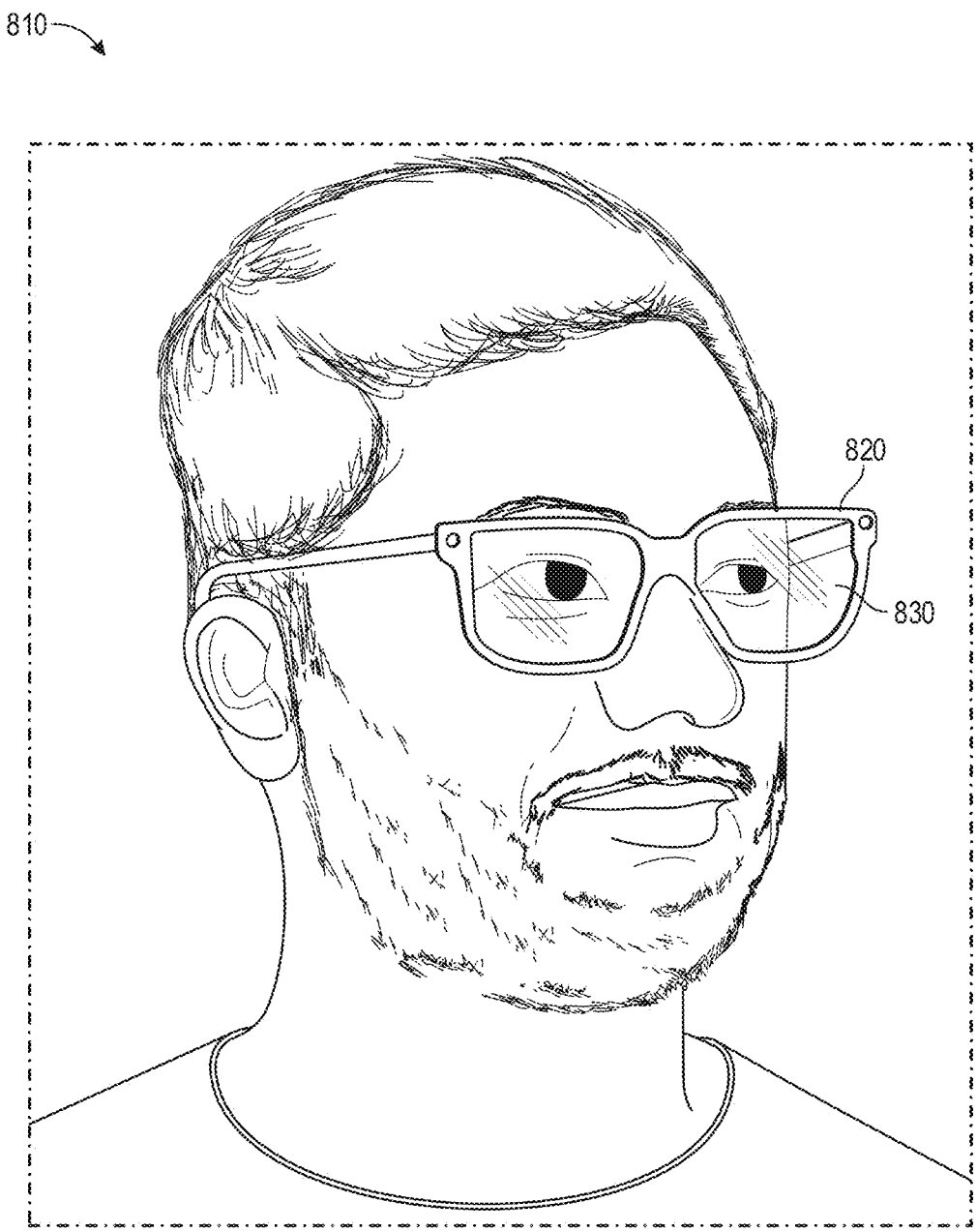

As another example, the eyewear generation module 519 computes a fit factor for each of the glasses by determining lens dimensions of each one of the plurality of physical glasses. For example, as shown in FIG. 8, the eyewear generation module 519 determines the lens dimension 830 of the augmented reality glasses 820. The lens dimension 830 shown in the image 810 of FIG. 8 is generated by scaling the lens dimension of the physical glasses based on the real-world scaling factor of the user's face. Namely, the lens dimension 830 is adjusted in size by an amount determined based on the real-world scaling factor of the user's face before being placed on the image 810 depicting the user's face. The eyewear generation module 519 determines the real-world physical measurements of the landmarks depicted in the image of the user's face and the smoothed depth map and then computes the fit factor for each of the glasses as a function of the lens dimensions and the real-world physical measurements of the landmarks. The eyewear generation module 519 ranks and sorts all of the physical glasses based on the computed fit factor and automatically selects one or a subset of the physical glasses having a top fit factor (e.g., a fit factor better than the rest) to present to the user.

In some examples, the eyewear generation module 519 displays a warning message in response to determining that a fit factor for each of a plurality of physical glasses fails to be satisfied. For example, if the facial dimensions of the user exceed a measurement (e.g., are too small or too large) of each of the glasses (e.g., the distance between the nose bridge and temple on the user's face is larger by a specified amount than a distance between a nose bridge portion and temple of the glasses), the eyewear generation module 519 displays the warning message.

Figure 9:
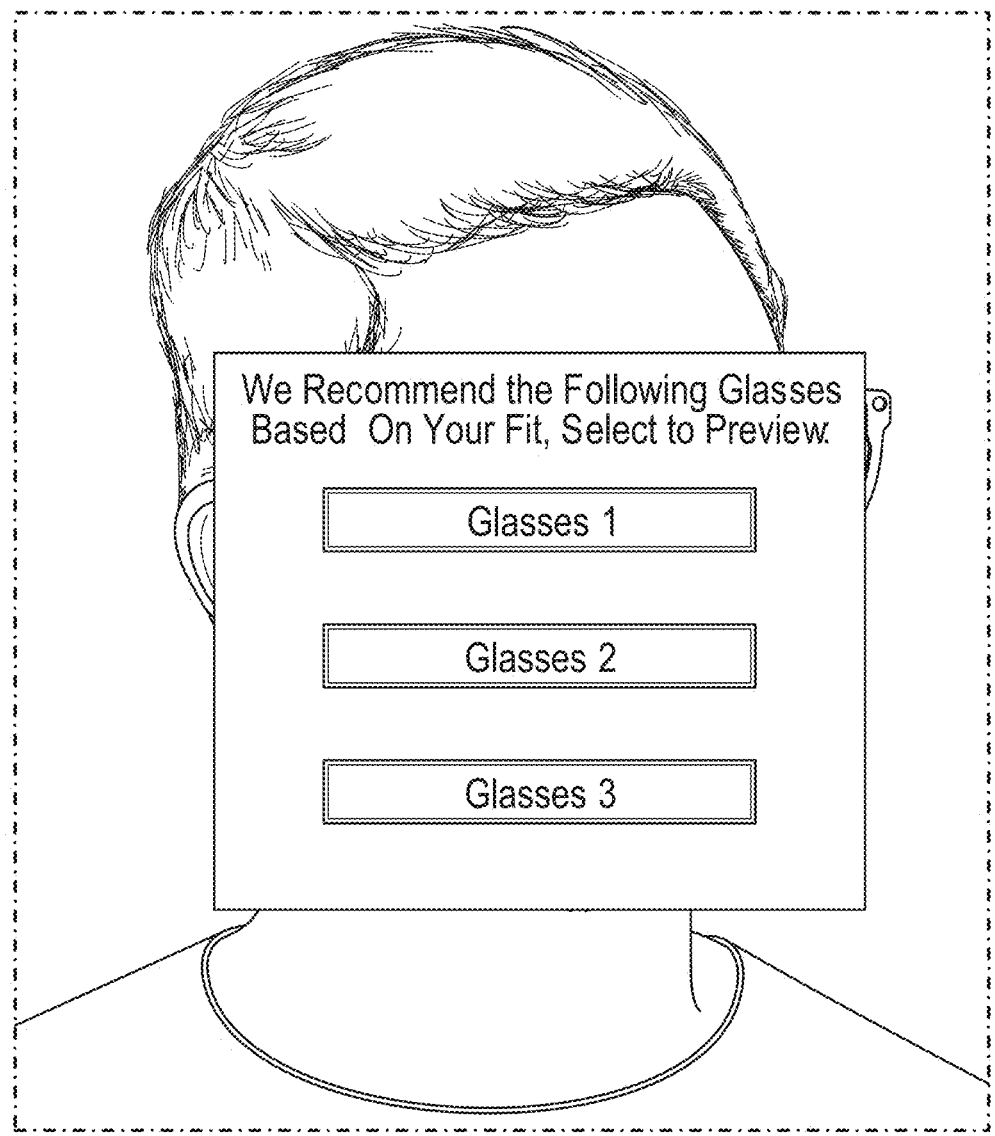

In some examples, the eyewear generation module 519 displays a prompt shown in FIG. 9 that lists the top ranked glasses. Namely, the eyewear generation module 519 selects a specified number of glasses (e.g., three glasses) that have an associated fit factor that is better than fit factors associated with a remaining set of glasses. The eyewear generation module 519 can receive a user selection of physical glasses among the listed set of physical glasses. In response, the eyewear generation module 519 scales the augmented reality element representing the physical glasses selected by the user and positions the scaled augmented reality element within the image or video feed depicting the user's face.

In some implementations, the image modification module 518 can deform the augmented reality element placed on top of the user's face in the image or video based on movement of the user's face. For example, the image modification module 518 can obtain rigid material properties associated with the augmented reality graphical element, such as by accessing the eyewear data 503. The image modification module 518 deforms a first portion of the augmented reality graphical element in response to determining that the rigid material properties correspond to a first rigidity amount. The image modification module 518 deforms a plurality of portions of the augmented reality graphical element in response to determining that the rigid material properties correspond to a second rigidity amount. In some cases, the first rigidity amount is smaller than the second rigidity amount. For example, if the glasses are more rigid, the image modification module 518 can bend or deform the nose bridge portion of the augmented reality element and the temples portion of the augmented reality element when positioned on the user's face relative to the default formation of the augmented reality element when not placed on the user's face. As another example, if the glasses are more flexible, the image modification module 518 can bend or deform only the temples portion of the augmented reality element when positioned on the user's face relative to the default formation of the augmented reality element when not placed on the user's face.

Figure 10A:
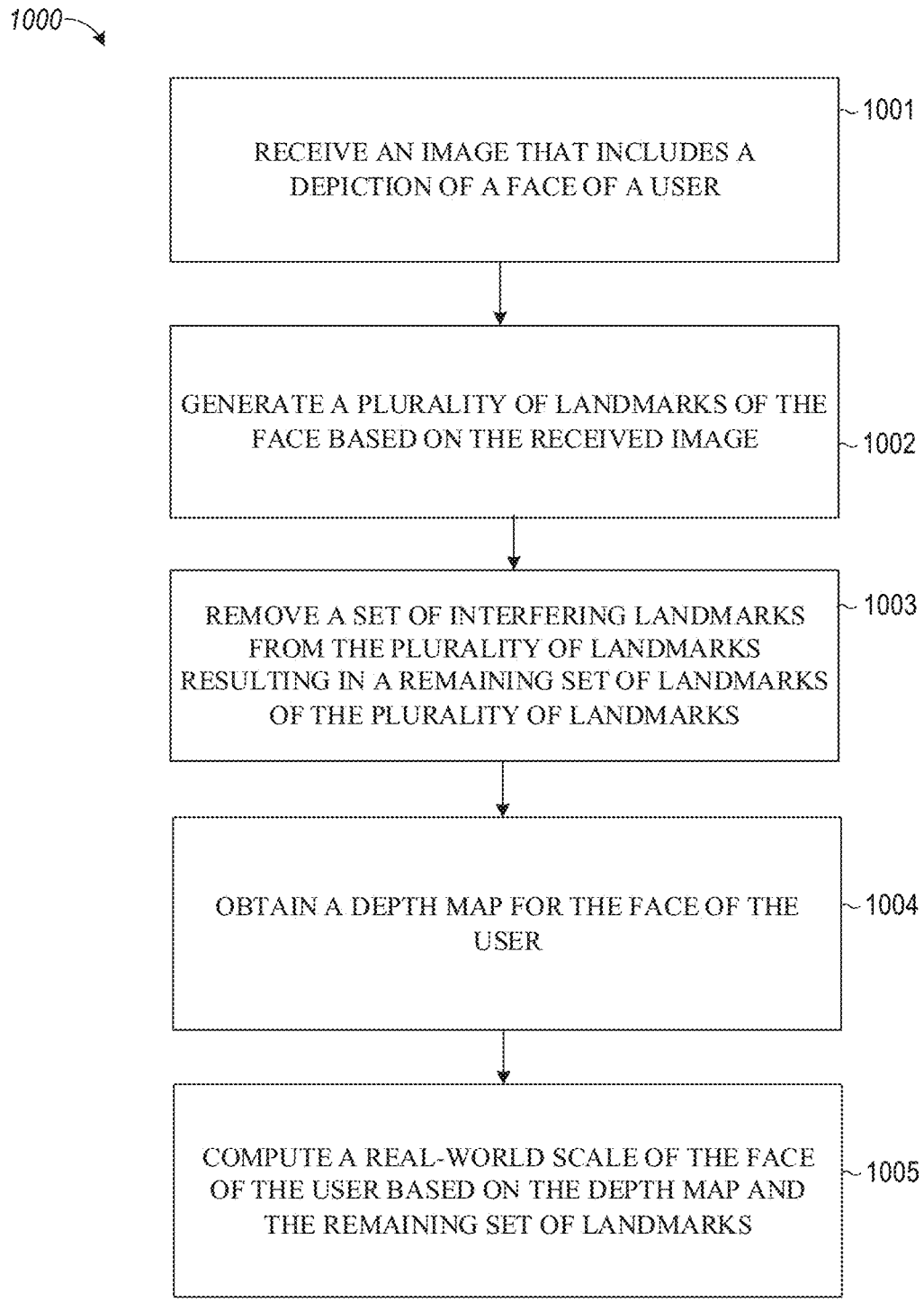
FIGS. 10A and 10B are flowcharts illustrating example operations of the messaging application server, according to examples.

FIG. 10A is a flowchart of a process 1000, in accordance with some example examples. Although the flowchart can describe the operations as a sequential process, many of the operations can be performed in parallel or concurrently. In addition, the order of the operations may be re-arranged. A process is terminated when its operations are completed. A process may correspond to a method, a procedure, and the like. The steps of methods may be performed in whole or in part, may be performed in conjunction with some or all of the steps in other methods, and may be performed by any number of different systems or any portion thereof, such as a processor included in any of the systems.

At operation 1001, a client device 102 receives an image that includes a depiction of a face of a user, as discussed above. For example, the true size estimation system 224 can capture an image that depicts one or more faces of one or more users (e.g., a plurality of users).

At operation 1002, the client device 102 generates a plurality of landmarks of the face based on the received image, as discussed above. As an example, the true size estimation system 224 can generate the landmarks by applying a machine learning technique to the image.

At operation 1003, the client device 102 removes a set of interfering landmarks from the plurality of landmarks resulting in a remaining set of landmarks of the plurality of landmarks, as discussed above.

At operation 1004, the client device 102 obtains a depth map for the face of the user, as discussed above.

At operation 1005, the client device 102 computes a real-world scale of the face of the user based on the depth map and the remaining set of landmarks, as discussed above.

Figure 10B:
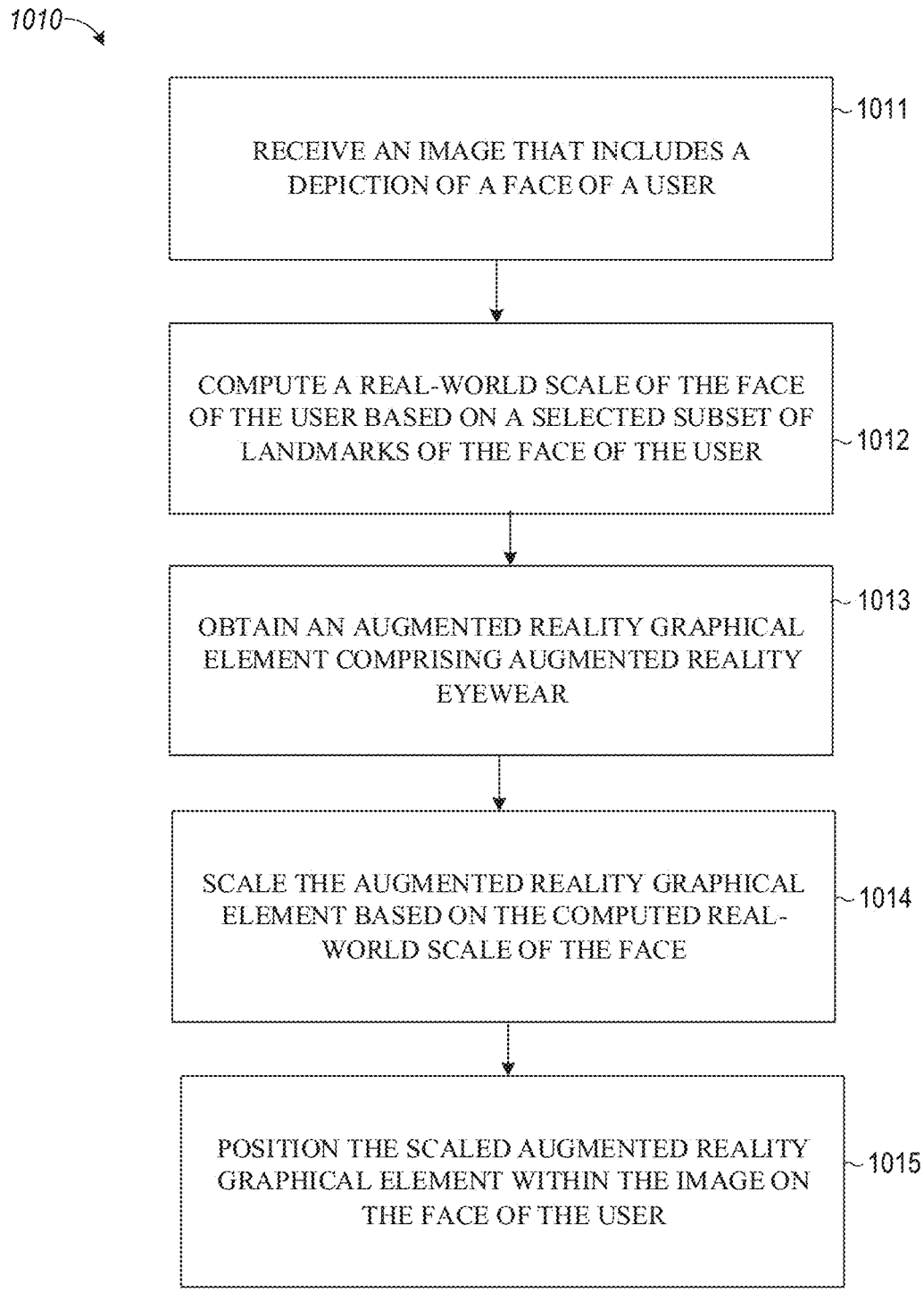

FIG. 10B is a flowchart of a process 1010, in accordance with some example examples. Although the flowchart can describe the operations as a sequential process, many of the operations can be performed in parallel or concurrently. In addition, the order of the operations may be re-arranged. A process is terminated when its operations are completed. A process may correspond to a method, a procedure, and the like. The steps of methods may be performed in whole or in part, may be performed in conjunction with some or all of the steps in other methods, and may be performed by any number of different systems or any portion thereof, such as a processor included in any of the systems.

At operation 1011, a client device 102 receives an image that includes a depiction of a face of a user, as discussed above.

At operation 1012, the client device 102 computes a real-world scale of the face of the user based on a selected subset of landmarks of the face of the user, as discussed above.

At operation 1013, the client device 102 obtains an augmented reality graphical element comprising augmented reality eyewear, as discussed above.

At operation 1014, the client device 102 scales the augmented reality graphical element based on the computed real-world scale of the face, as discussed above.

At operation 1015, the client device 102 positions the scaled augmented reality graphical element within the image on the face of the user.

Machine Architecture

Figure 11:
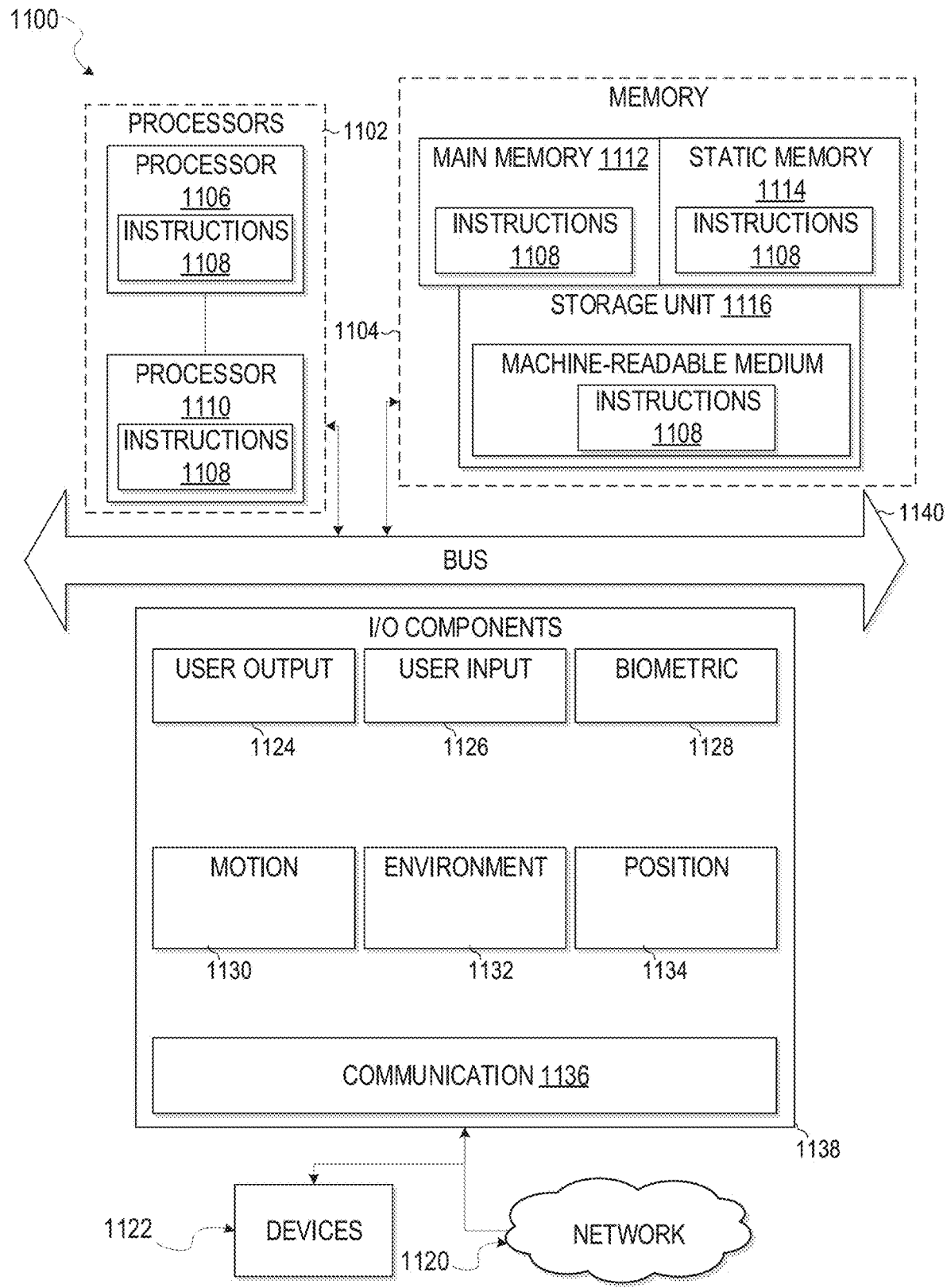
FIG. 11 is a diagrammatic representation of a machine in the form of a computer system within which a set of instructions may be executed for causing the machine to perform any one or more of the methodologies discussed herein, in accordance with some examples.

FIG. 11 is a diagrammatic representation of the machine 1100 within which instructions 1108 (e.g., software, a program, an application, an applet, an app, or other executable code) for causing the machine 1100 to perform any one or more of the methodologies discussed herein may be executed. For example, the instructions 1108 may cause the machine 1100 to execute any one or more of the methods described herein. The instructions 1108 transform the general, non-programmed machine 1100 into a particular machine 1100 programmed to carry out the described and illustrated functions in the manner described. The machine 1100 may operate as a standalone device or may be coupled (e.g., networked) to other machines. In a networked deployment, the machine 1100 may operate in the capacity of a server machine or a client machine in a server-client network environment, or as a peer machine in a peer-to-peer (or distributed) network environment. The machine 1100 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smartphone, a mobile device, a wearable device (e.g., a smartwatch), a smart home device (e.g., a smart appliance), other smart devices, a web appliance, a network router, a network switch, a network bridge, or any machine capable of executing the instructions 1108, sequentially or otherwise, that specify actions to be taken by the machine 1100. Further, while only a single machine 1100 is illustrated, the term "machine" shall also be taken to include a collection of machines that individually or jointly execute the instructions 1108 to perform any one or more of the methodologies discussed herein. The machine 1100, for example, may comprise the client device 102 or any one of a number of server devices forming part of the messaging server system 108. In some examples, the machine 1100 may also comprise both client and server systems, with certain operations of a particular method or algorithm being performed on the server-side and with certain operations of the particular method or algorithm being performed on the client-side.

The machine 1100 may include processors 1102, memory 1104, and input/output (I/O) components 1138, which may be configured to communicate with each other via a bus 1140. In an example, the processors 1102 (e.g., a Central Processing Unit (CPU), a Reduced Instruction Set Computing (RISC) Processor, a Complex Instruction Set Computing (CISC) Processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, a processor 1106 and a processor 1110 that execute the instructions 1108. The term "processor" is intended to include multi-core processors that may comprise two or more independent processors (sometimes referred to as "cores") that may execute instructions contemporaneously. Although FIG. 11 shows multiple processors 1102, the machine 1100 may include a single processor with a single-core, a single processor with multiple cores (e.g., a multi-core processor), multiple processors with a single core, multiple processors with multiples cores, or any combination thereof.

The memory 1104 includes a main memory 1112, a static memory 1114, and a storage unit 1116, all accessible to the processors 1102 via the bus 1140. The main memory 1104, the static memory 1114, and the storage unit 1116 store the instructions 1108 embodying any one or more of the methodologies or functions described herein. The instructions 1108 may also reside, completely or partially, within the main memory 1112, within the static memory 1114, within machine-readable medium 1118 within the storage unit 1116, within at least one of the processors 1102 (e.g., within the processor's cache memory), or any suitable combination thereof, during execution thereof by the machine 1100.

The I/O components 1138 may include a wide variety of components to receive input, provide output, produce output, transmit information, exchange information, capture measurements, and so on. The specific I/O components 1138 that are included in a particular machine will depend on the type of machine. For example, portable machines such as mobile phones may include a touch input device or other such input mechanisms, while a headless server machine will likely not include such a touch input device. It will be appreciated that the I/O components 1138 may include many other components that are not shown in FIG. 11. In various examples, the I/O components 1138 may include user output components 1124 and user input components 1126. The user output components 1124 may include visual components (e.g., a display such as a plasma display panel (PDP), a light-emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The user input components 1126 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and force of touches or touch gestures, or other tactile input components), audio input components (e.g., a microphone), and the like.

In further examples, the I/O components 1138 may include biometric components 1128, motion components 1130, environmental components 1132, or position components 1134, among a wide array of other components. For example, the biometric components 1128 include components to detect expressions (e.g., hand expressions, facial expressions, vocal expressions, body gestures, or eye-tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 1130 include acceleration sensor components (e.g., accelerometer), gravitation sensor components, rotation sensor components (e.g., gyroscope).

The environmental components 1132 include, for example, one or cameras (with still image/photograph and video capabilities), illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment.

With respect to cameras, the client device 102 may have a camera system comprising, for example, front cameras on a front surface of the client device 102 and rear cameras on a rear surface of the client device 102. The front cameras may, for example, be used to capture still images and video of a user of the client device 102 (e.g., "selfies"), which may then be augmented with augmentation data (e.g., filters) described above. The rear cameras may, for example, be used to capture still images and videos in a more traditional camera mode, with these images similarly being augmented with augmentation data. In addition to front and rear cameras, the client device 102 may also include a 360° camera for capturing 360° photographs and videos.

Further, the camera system of a client device 102 may include dual rear cameras (e.g., a primary camera as well as a depth-sensing camera), or even triple, quad or penta rear camera configurations on the front and rear sides of the client device 102. These multiple cameras systems may include a wide camera, an ultra-wide camera, a telephoto camera, a macro camera, and a depth sensor, for example.

The position components 1134 include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1138 further include communication components 1136 operable to couple the machine 1100 to a network 1120 or devices 1122 via respective coupling or connections. For example, the communication components 1136 may include a network interface component or another suitable device to interface with the network 1120. In further examples, the communication components 1136 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1122 may be another machine or any of a wide variety of peripheral devices (e.g., a peripheral device coupled via a USB).

Moreover, the communication components 1136 may detect identifiers or include components operable to detect identifiers. For example, the communication components 1136 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1136, such as location via Internet Protocol (IP) geolocation, location via Wi-Fi® signal triangulation, location via detecting an NFC beacon signal that may indicate a particular location, and so forth.

The various memories (e.g., main memory 1112, static memory 1114, and memory of the processors 1102) and storage unit 1116 may store one or more sets of instructions and data structures (e.g., software) embodying or used by any one or more of the methodologies or functions described herein. These instructions (e.g., the instructions 1108), when executed by processors 1102, cause various operations to implement the disclosed examples.

The instructions 1108 may be transmitted or received over the network 1120, using a transmission medium, via a network interface device (e.g., a network interface component included in the communication components 1136) and using any one of several well-known transfer protocols (e.g., hypertext transfer protocol (HTTP)). Similarly, the instructions 1108 may be transmitted or received using a transmission medium via a coupling (e.g., a peer-to-peer coupling) to the devices 1122.

Software Architecture

Figure 12:
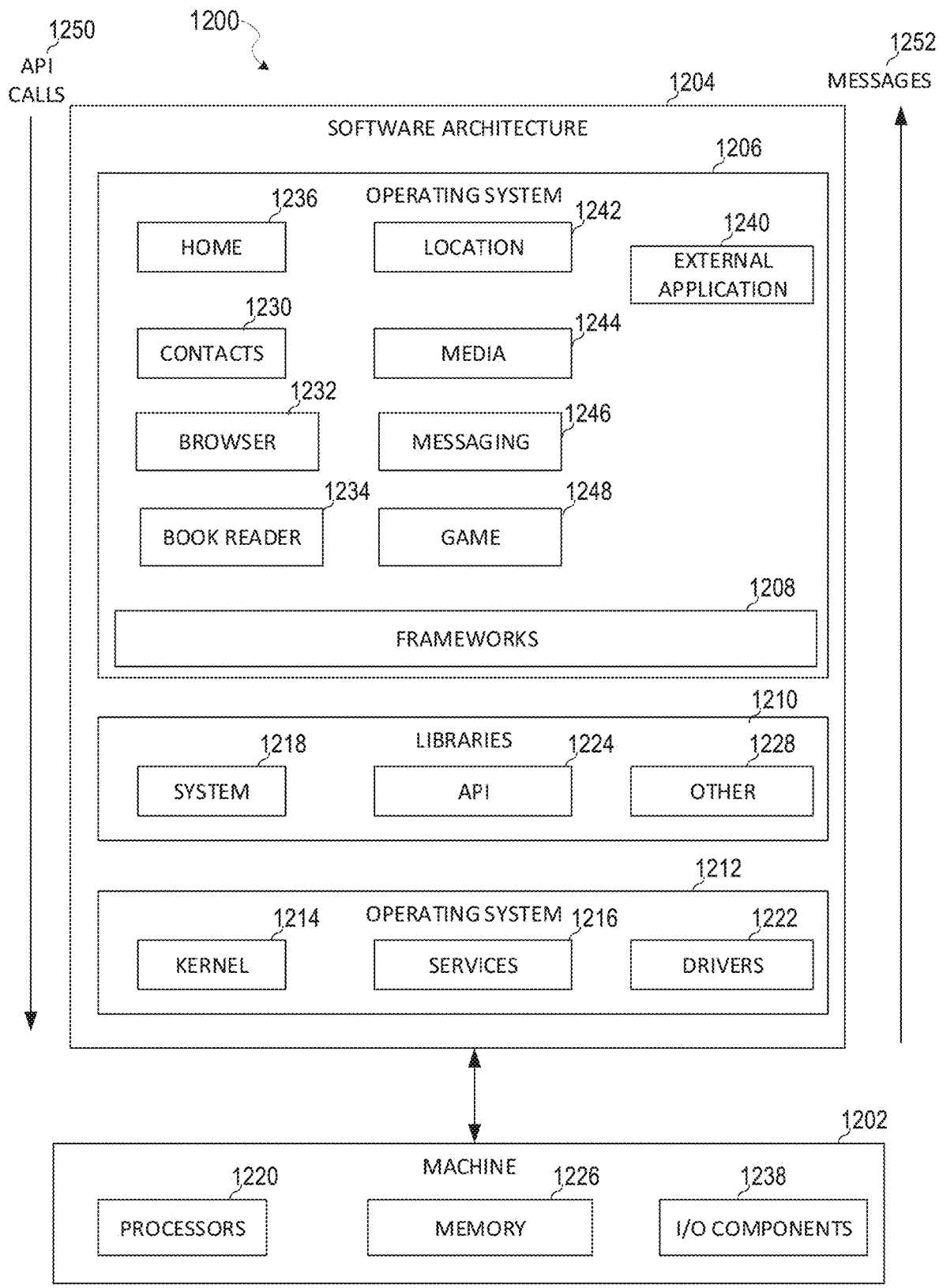
FIG. 12 is a block diagram showing a software architecture within which examples may be implemented.

FIG. 12 is a block diagram 1200 illustrating a software architecture 1204, which can be installed on any one or more of the devices described herein. The software architecture 1204 is supported by hardware such as a machine 1202 that includes processors 1220, memory 1226, and I/O components 1238. In this example, the software architecture 1204 can be conceptualized as a stack of layers, where each layer provides a particular functionality. The software architecture 1204 includes layers such as an operating system 1212, libraries 1210, frameworks 1208, and applications 1206. Operationally, the applications 1206 invoke API calls 1250 through the software stack and receive messages 1252 in response to the API calls 1250.

The operating system 1212 manages hardware resources and provides common services. The operating system 1212 includes, for example, a kernel 1214, services 1216, and drivers 1222. The kernel 1214 acts as an abstraction layer between the hardware and the other software layers. For example, the kernel 1214 provides memory management, processor management (e.g., scheduling), component management, networking, and security settings, among other functionality. The services 1216 can provide other common services for the other software layers. The drivers 1222 are responsible for controlling or interfacing with the underlying hardware. For instance, the drivers 1222 can include display drivers, camera drivers, BLUETOOTH® or BLUETOOTH® Low Energy drivers, flash memory drivers, serial communication drivers (e.g., USB drivers), WI-FI® drivers, audio drivers, power management drivers, and so forth.

The libraries 1210 provide a common low-level infrastructure used by the applications 1206. The libraries 1210 can include system libraries 1218 (e.g., C standard library) that provide functions such as memory allocation functions, string manipulation functions, mathematic functions, and the like. In addition, the libraries 1210 can include API libraries 1224 such as media libraries (e.g., libraries to support presentation and manipulation of various media formats such as Moving Picture Experts Group-4 (MPEG4), Advanced Video Coding (H.264 or AVC), Moving Picture Experts Group Layer-3 (MP3), Advanced Audio Coding (AAC), Adaptive Multi-Rate (AMR) audio codec, Joint Photographic Experts Group (JPEG or JPG), or Portable Network Graphics (PNG)), graphics libraries (e.g., an OpenGL framework used to render in two dimensions (2D) and three dimensions (3D) in a graphic content on a display), database libraries (e.g., SQLite to provide various relational database functions), web libraries (e.g., WebKit to provide web browsing functionality), and the like. The libraries 1210 can also include a wide variety of other libraries 1228 to provide many other APIs to the applications 1206.

The frameworks 1208 provide a common high-level infrastructure that is used by the applications 1206. For example, the frameworks 1208 provide various graphical user interface (GUI) functions, high-level resource management, and high-level location services. The frameworks 1208 can provide a broad spectrum of other APIs that can be used by the applications 1206, some of which may be specific to a particular operating system or platform.

In an example, the applications 1206 may include a home application 1236, a contacts application 1230, a browser application 1232, a book reader application 1234, a location application 1242, a media application 1244, a messaging application 1246, a game application 1248, and a broad assortment of other applications such as a external application 1240. The applications 1206 are programs that execute functions defined in the programs. Various programming languages can be employed to create one or more of the applications 1206, structured in a variety of manners, such as object-oriented programming languages (e.g., Objective-C, Java, or C++) or procedural programming languages (e.g., C or assembly language). In a specific example, the external application 1240 (e.g., an application developed using the ANDROID™ or IOS™ software development kit (SDK) by an entity other than the vendor of the particular platform) may be mobile software running on a mobile operating system such as IOS™, ANDROID™, WINDOWS® Phone, or another mobile operating system. In this example, the external application 1240 can invoke the API calls 1250 provided by the operating system 1212 to facilitate functionality described herein.

Glossary

"Carrier signal" refers to any intangible medium that is capable of storing, encoding, or carrying instructions for execution by the machine, and includes digital or analog communications signals or other intangible media to facilitate communication of such instructions. Instructions may be transmitted or received over a network using a transmission medium via a network interface device.

"Client device" refers to any machine that interfaces to a communications network to obtain resources from one or more server systems or other client devices. A client device may be, but is not limited to, a mobile phone, desktop computer, laptop, portable digital assistants (PDAs), smartphones, tablets, ultrabooks, netbooks, laptops, multi-processor systems, microprocessor-based or programmable consumer electronics, game consoles, set-top boxes, or any other communication device that a user may use to access a network.

"Communication network" refers to one or more portions of a network that may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other types of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long-range protocols, or other data transfer technology.

"Component" refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions.

Components may constitute either software components (e.g., code embodied on a machine-readable medium) or hardware components. A "hardware component" is a tangible unit capable of performing certain operations and may be configured or arranged in a certain physical manner. In various examples, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a field-programmable gate array (FPGA) or an application specific integrated circuit (ASIC). A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software), may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein.

Considering examples in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In examples in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors 1102 or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some examples, the processors or processor-implemented components may be located in a single geographic location (e.g., within a home environment, an office environment, or a server farm). In other examples, the processors or processor-implemented components may be distributed across a number of geographic locations.

"Computer-readable storage medium" refers to both machine-storage media and transmission media. Thus, the terms include both storage devices/media and carrier waves/modulated data signals. The terms "machine-readable medium," "computer-readable medium" and "device-readable medium" mean the same thing and may be used interchangeably in this disclosure.

"Ephemeral message" refers to a message that is accessible for a time-limited duration. An ephemeral message may be a text, an image, a video and the like. The access time for the ephemeral message may be set by the message sender. Alternatively, the access time may be a default setting or a setting specified by the recipient. Regardless of the setting technique, the message is transitory.

"Machine storage medium" refers to a single or multiple storage devices and media (e.g., a centralized or distributed database, and associated caches and servers) that store executable instructions, routines and data. The term shall accordingly be taken to include, but not be limited to, solid-state memories, and optical and magnetic media, including memory internal or external to processors. Specific examples of machine-storage media, computer-storage media and device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks The terms "machine-storage medium," "device-storage medium," "computer-storage medium" mean the same thing and may be used interchangeably in this disclosure. The terms "machine-storage media," "computer-storage media," and "device-storage media" specifically exclude carrier waves, modulated data signals, and other such media, at least some of which are covered under the term "signal medium."

"Non-transitory computer-readable storage medium" refers to a tangible medium that is capable of storing, encoding, or carrying the instructions for execution by a machine.

"Signal medium" refers to any intangible medium that is capable of storing, encoding, or carrying the instructions for execution by a machine and includes digital or analog communications signals or other intangible media to facilitate communication of software or data. The term "signal medium" shall be taken to include any form of a modulated data signal, carrier wave, and so forth. The term "modulated data signal" means a signal that has one or more of its characteristics set or changed in such a matter as to encode information in the signal. The terms "transmission medium" and "signal medium" mean the same thing and may be used interchangeably in this disclosure.

Changes and modifications may be made to the disclosed examples without departing from the scope of the present disclosure. These and other changes or modifications are intended to be included within the scope of the present disclosure, as expressed in the following claims.

What is claimed is:

1. A method comprising:
   receiving, by one or more processors of a user device, an image that includes a depiction of a face of a user;
   computing a real-world scale of the face of the user based on a selected subset of landmarks of the face of the user;
   obtaining an augmented reality graphical element comprising augmented reality eyewear;
   changing a size of the augmented reality graphical element based on the computed real-world scale of the face as a function of a distance between the face of the user and the user device, the size of the augmented reality graphical element being adjusted to be a first value in response to determining that the distance between the face of the user and the user device is a first amount, the size of the augmented reality graphical element being decreased to a second value that is smaller than the first value in response to determining that the distance between the face of the user and the user device has increased to a second amount greater than the first amount; and
   positioning the resized augmented reality graphical element within the image on the face of the user.

2. The method of claim 1, further comprising:
   retrieving physical size information of the augmented reality element;
   computing an adjustment factor associated with the physical size information based on the computed real-world scale of the face; and
   modifying a size of the augmented reality graphical element based on the adjustment factor.

3. The method of claim 1, further comprising:
   obtaining rigid material properties associated with the augmented reality graphical element; and
   displaying, based on the rigid material properties, the augmented reality graphical element in the image.

4. The method of claim 3, further comprising:
   deforming a first portion of the augmented reality graphical element in response to determining that the rigid material properties correspond to a first rigidity amount; and
   deforming a plurality of portions of the augmented reality graphical element in response to determining that the rigid material properties correspond to a second rigidity amount.

5. The method of claim 1, wherein computing the real-world scale of the face of the user comprises:
   computing a first instance of the real-world scale of the face of the user based on a first set of landmarks of the subset of the landmarks of the face of the user at a first point in time during a first portion of a video captured by the user device; and
   computing a second instance of the real-world scale of the face of the user based on a second set of landmarks of the subset of the landmarks of the face of the user at a second point in time during a second portion of a video captured by the user device, the second set of landmarks used to compute the second instance of the real-world scale of the face of the user being different from the first set of landmarks used to compute the first instance of the real-world scale of the face of the user.

6. The method of claim 1, further comprising:
   determining a topology of the face of the user based on the selected subset of landmarks; and
   positioning the resized augmented reality graphical element within the image on the face of the user based on the topology.

7. The method of claim 6, further comprising positioning a nose bridge portion of the augmented reality graphical element a predetermined distance above a nose bridge landmark within the topology.

8. The method of claim 1, further comprising:
   identifying a plurality of physical glasses;
   retrieving a plurality of physical measurements of the plurality of physical glasses; and
   computing a fit factor for each of the physical glasses based on the physical measurements and the computed real-world scale of the face of the user.

9. The method of claim 8, further comprising:
   ranking the physical glasses based on a respective fit factor of each of the physical glasses; and
   generating, based on the ranking, a recommendation of an eyewear augmented reality element for one or more physical glasses associated with one or more top ranks.

10. The method of claim 9, further comprising positioning the eyewear augmented reality element within the image on the face of the user in response to a received input.

11. The method of claim 8, further comprising computing a given fit factor for a given one of the plurality of physical glasses by:
    determining a first distance between a nose bridge portion of the given one of the plurality of physical glasses and a temples portion of the given one of the plurality of physical glasses;
    computing a second distance in the computed real-world scale of the face of the user between a nose bridge and a cheek bone or temple of the face of the user; and
    computing the fit factor as a function of the first distance and the second distance.

12. The method of claim 8, further comprising computing a given fit factor for a given one of the plurality of physical glasses by:
    determining lens dimensions of the given one of the plurality of physical glasses; and
    computing the fit factor as a function of the lens dimensions.

13. The method of claim 1, further comprising:
computing visibility and stability parameters for each of the selected subset of landmarks of the face of the user, the visibility parameter specifying a score representing how much of each of the selected subset of landmarks of the face of the user that is visible in the image, the visibility parameter being proportional to an amount of overlap between each of the selected subset of landmarks of the face of the user and a predetermined portion of a three-dimensional facial model, the stability parameter indicating how much each of the selected subset of landmarks of the face of the user moves over a threshold number of frames of a video.

14. The method of claim 13, further comprising:
selecting a set of top landmarks that is each associated with a visibility and stability score greater than respective visibility and stability scores of a remaining set of landmarks.

15. The method of claim 14, further comprising:
determining a type associated with the augmented reality eyewear;
obtaining a threshold quantity of landmarks associated with the type of the augmented reality eyewear; and
using the threshold quantity of landmarks to limit a quantity of landmarks that are included in the set of top landmarks.

16. The method of claim 1, further comprising:
selecting a style for the augmented reality eyewear based on one or more attributes associated with the user.

17. The method of claim 1, further comprising:
detecting a finger of the user in a video captured by the user device;
determining that the finger overlaps a nose portion of the augmented reality graphical element;
in response to determining that the finger overlaps the nose portion of the augmented reality graphical element, determining a direction of movement of the finger relative to eyebrows of the user; and
moving the augmented reality graphical element relative to the nose portion by a specified amount based on an amount and direction of movement of the finger relative to eyebrows of the user.

18. The method of claim 1, further comprising:
displaying a warning message in response to determining that a fit factor for each of a plurality of physical glasses fails to be satisfied.

19. A system comprising:
at least one processor, and
a memory component having instructions stored thereon, when executed by the at least one processor, causes the at least one processor to perform operations comprising:
receiving, by a user device, an image that includes a depiction of a face of a user;
computing a real-world scale of the face of the user based on a selected subset of landmarks of the face of the user;
obtaining an augmented reality graphical element comprising augmented reality eyewear;
changing a size of the augmented reality graphical element based on the computed real-world scale of the face as a function of a distance between the face of the user and the user device, the size of the augmented reality graphical element being adjusted to be a first value in response to determining that the distance between the face of the user and the user device is a first amount, the size of the augmented reality graphical element being decreased to a second value that is smaller than the first value in response to determining that the distance between the face of the user and the user device has increased to a second amount greater than the first amount; and
positioning the resized augmented reality graphical element within the image on the face of the user.

20. A non-transitory computer-readable medium having stored thereon, instructions when executed by at least one processor, causes the at least one processor to perform operations comprising:
receiving, by a user device, an image that includes a depiction of a face of a user;
computing a real-world scale of the face of the user based on a selected subset of landmarks of the face of the user;
obtaining an augmented reality graphical element comprising augmented reality eyewear;
changing a size of the augmented reality graphical element based on the computed real-world scale of the face as a function of a distance between the face of the user and the user device, the size of the augmented reality graphical element being adjusted to be a first value in response to determining that the distance between the face of the user and the user device is a first amount, the size of the augmented reality graphical element being decreased to a second value that is smaller than the first value in response to determining that the distance between the face of the user and the user device has increased to a second amount greater than the first amount; and
positioning the resized augmented reality graphical element within the image on the face of the user.

\* \* \* \* \*

UNITED STATES PATENT AND TRADEMARK OFFICE
CERTIFICATE OF CORRECTION

| | |
|---|---|
| PATENT NO. | : 12,067,804 B2 |
| APPLICATION NO. | : 17/208208 |
| DATED | : August 20, 2024 |
| INVENTOR(S) | : Assouline et al. |

Page 1 of 1

It is certified that error appears in the above-identified patent and that said Letters Patent is hereby corrected as shown below:

In the Claims

In Column 35, Line 47, in Claim 19, delete "processor," and insert --processor;-- therefor Signed and Sealed this
Thirtieth Day of September, 2025

John A. Squires
*Director of the United States Patent and Trademark Office*